United States Patent
Knegtel et al.

(10) Patent No.: US 8,129,381 B2
(45) Date of Patent: Mar. 6, 2012

(54) CASPASE INHIBITORS AND USES THEREOF

(75) Inventors: Ronald Knegtel, Abingdon (GB); Michael Mortimore, Burford (GB); John Studley, Abingdon (GB); David Millan, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 253 days.

(21) Appl. No.: 12/464,380

(22) Filed: May 12, 2009

(65) Prior Publication Data

US 2009/0281128 A1    Nov. 12, 2009

Related U.S. Application Data

(62) Division of application No. 10/609,147, filed on Jun. 27, 2003, now Pat. No. 7,553,852.

(60) Provisional application No. 60/392,592, filed on Jun. 28, 2002, provisional application No. 60/435,073, filed on Dec. 20, 2002.

(51) Int. Cl.
*A01N 43/58* (2006.01)
*A61K 31/50* (2006.01)
*C07D 239/72* (2006.01)

(52) U.S. Cl. .................................. 514/248; 544/283
(58) Field of Classification Search .............. 544/283; 514/248
See application file for complete search history.

(56) References Cited

U.S. PATENT DOCUMENTS

| | | | |
|---|---|---|---|
| 4,728,647 A | 3/1988 | Benavides et al. | |
| 5,656,627 A | 8/1997 | Bemis et al. | |
| 5,716,929 A | 2/1998 | Bemis et al. | |
| 5,756,466 A | 5/1998 | Bemis et al. | |
| 5,847,135 A | 12/1998 | Bemis et al. | |
| 5,973,111 A | 10/1999 | Bemis et al. | |
| 6,025,147 A | 2/2000 | Bemis et al. | |
| 6,103,711 A | 8/2000 | Bemis et al. | |
| 6,420,522 B1 | 7/2002 | Bemis et al. | |
| 6,525,076 B1 | 2/2003 | Zhu et al. | |
| 2003/0162993 A1 | 8/2003 | Mortimore et al. | |
| 2004/0019017 A1 | 1/2004 | Mortimore et al. | |
| 2004/0048797 A1 | 3/2004 | Miller et al. | |
| 2004/0242494 A1 | 12/2004 | Brenchley et al. | |

FOREIGN PATENT DOCUMENTS

| | | |
|---|---|---|
| DE | 232699 | 2/1986 |
| EP | 0761680 A2 | 12/1997 |
| EP | 1203766 A2 | 5/2002 |
| WO | 9535308 A1 | 12/1995 |
| WO | 9640647 A1 | 12/1996 |
| WO | 9722619 A2 | 6/1997 |
| WO | 9816502 A1 | 4/1998 |
| WO | 9816505 A1 | 4/1998 |
| WO | 98/18781 A2 | 5/1998 |
| WO | 00/67746 A1 | 11/2000 |
| WO | 0068188 A1 | 11/2000 |
| WO | 0142216 | 6/2001 |
| WO | WO 0142216 * | 6/2001 |
| WO | 01/94351 A1 | 12/2001 |
| WO | 03068242 | 8/2003 |
| WO | 2004/002961 A1 | 1/2004 |
| WO | 2004058718 A1 | 7/2004 |
| WO | 2006057961 A1 | 6/2006 |

OTHER PUBLICATIONS

Prokai-Tatrai, K. et al., "Prodrugs to Enhance Central Nervous System Effects of TRH-like Peptide pGlu-Glu-Pro-NH2," Bioorg. Med. Chem. Lett., 13,1011-1014, (2003).
Narasimhan, R.S. "Synthetic Application of Lithiation Reactions; IX. A Simplified Synthesis of Isocoumarin," Synthesis, 12(797), (1975).
Kinder, M.A., et al. "Solid State Photochemistry of Isocoumarins and Isothiocoumarins," Tetrahedron 56, 6763-6767 (2000).
Revesz, L., et al. "Synthesis of P1 Aspartate-Based Peptide Acyloxymethyl and Fluoromethyl Ketones as Inhibitors of Interleukin-1β-Converting Enzyme," Tetrahedron Letters, 35(52): 9693-9696,(1994).
Aug. 31, 2005 Office Action from U.S. Appl. No. 10/743,563.
Oct. 3, 2006 Office Action from U.S. Appl. No. 10/743,563.
Jul. 9, 2007 Examiner's Amendment from U.S. Appl. No. 10/743,563.
Jun. 12, 2003 Office Action from U.S. Appl. No. 10/166,437.
Feb. 26, 2004 Office Action from U.S. Appl. No. 10/166,437.
Jan. 26, 2007 Office Action from U.S. Appl. No. 10/166,437.
Golec, et al. "Structure-Based Design of Non-Peptidic Pyridone Aldehydes as inhibitors of interleukin-1β Converting Enzyme", Bioorganic & Medicinal Chemistry Letters, 7(17): 2181-2186, (1997).
Semple, et al. "Peptidomimetic Aminomethylene Ketone Inhibitors of Interleukin-1β Converting Enzyme (ICE)", Bioorganic & medicinal Chemistry Letters, 8, 959-964, (1998).
Semple, G., et al. "Pyridone-Based Peptidomimetic Inhibitors of Interleukin-1β -Converting Enzyme (ICE)," Bioorganic & Medicinal Chem. Letters, 7(10):1337-1342 (1997).

(Continued)

*Primary Examiner* — Paul V. Ward
(74) *Attorney, Agent, or Firm* — Jennifer G. Che; Lisa A. Dixon; Vertex Pharmaceuticals Incorporated

(57) ABSTRACT

The present invention relates to compounds of formula I:

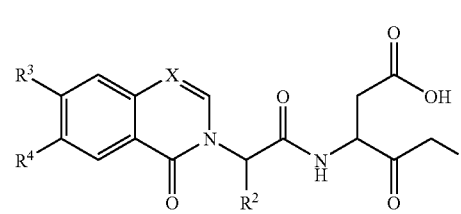

useful as inhibitors of caspases. The present invention also provides pharmaceutically acceptable compositions comprising said compounds, processes for preparing the compounds, and methods of using the compounds and compositions in the treatment of various diseases, conditions, or disorders.

2 Claims, No Drawings

OTHER PUBLICATIONS

Livingston, D.J. "In Vitro and In Vivo Studies of Ice Inhibitors," J. of Cell. Biochem., 64(1):19-26 (1997).

Husain, M. I., et al. "Some New 2-Aryloxymethyl-3-alpha-substituted Carboxymethyl-6,8-substituted-4-Quinazolones As Possible Anticonvulsants,", Pharmazie, 37(6):408-410, (1982).

Hussain, M., Imtiaz, et al. "Some Newer Quinazolones as Possible Anticonvulsants," J. Chem. Soc. Pak, 6 (4):211-215, (1984).

Cannone, P., et al. "Synthesis of chiral 3-substituted 2,4(1H,3H)-quinazolinediones," Heterocycles, 36(6):1305-1314, (1993).

Gouilleux, L, et al. "Solid Phase Synthesis of Chiral 3-substituted Quinazoline-2, 4-diones," Tetrahedron, Letters, 37 (39):7031-7034, (1996).

Gordeev, M. F., et al. "A General and Efficient Solid Phase Synthesis of Quinazoline-2, 4-diones," Tetrahedron Letters, 38(10)1729-1732, (1997).

* cited by examiner

CASPASE INHIBITORS AND USES THEREOF

CROSS REFERENCE TO RELATED APPLICATIONS

This application is a divisional of U.S. patent application Ser. No. 10/609,147, filed Jun. 27, 2003; which claims the benefit of U.S. Provisional Application 60/392,592 filed Jun. 28, 2002 and U.S. Provisional Application 60/435,073, filed Dec. 20, 2002, the contents of which are incorporated herein by reference.

FIELD OF THE INVENTION

This invention is in the field of medicinal chemistry and relates to compounds, and pharmaceutical compositions thereof, that inhibit caspases that mediate cell apoptosis and inflammation. The invention also relates to processes for preparing the compounds and to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 281, 1283-1312 (1998); Ellis et al., *Ann. Rev. Cell. Biol.*, 7, 663 (1991)).

Caspases are a family of cysteine protease enzymes that are key mediators in the signaling pathways for apoptosis and cell disassembly (Thornberry, *Chem. Biol.*, 5, R97-R103 (1998)). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1 β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, 5 and 13, have been shown to prefer hydrophobic aromatic amino acids at position 4 on the N-terminal side of the cleavage site. Another group that includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, 5 and 13. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon-γ inducing factor (IGIF) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector caspases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$—[P4]-[P3]-[P2]—$CH(R)$ $CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J. Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improved survival after endotoxic shock. Yaoita et al., *Circulation*, 97, 276 (1998); Endres et al., *J Cerebral Blood Flow and Metabolism*, 18, 238, (1998); Cheng et al., *J. Clin. Invest.*, 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic inhibitors have been reported. Amongst these, inhibitors where the P3 amino acid has been replaced by derivatives of 3-aminopyridin-2-ones and 5-aminopyrimidin-4-ones have received much attention (U.S. Pat. No. 5,756,466 (Bemis et al.); Dolle et al. *J. Med. Chem.* 39, 2438, (1996); Golec et al. *Bioorg. Med. Chem. Lett.* 7, 2181, (1997); Semple et al, *Biorg. Med. Chem. Lett.* 7, 1337, (1997) involving compounds of general structure:

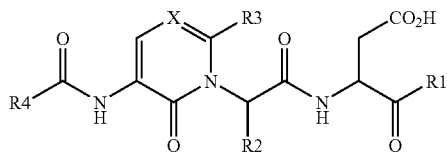

wherein $R_1$-$R_4$ and X are various groups.

Due to the inherent problems of the peptidic inhibitors, there continues to be a need for small molecule, nonpeptide caspase inhibitors that are potent, stable, and penetrate membranes to provide effective inhibition of apoptosis in vivo. Such compounds would be extremely useful in treating the aforementioned diseases where caspase enzymes play a role. WO 01/42216 discloses caspase inhibitors and uses thereof. The present invention provides a selection over the WO 01/42216 disclosure.

SUMMARY OF THE INVENTION

The present invention provides a compound of formula I:

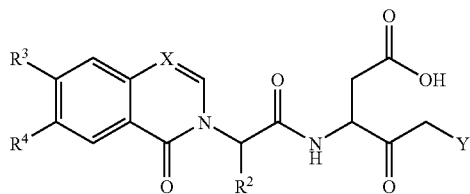

wherein:
X is CH or N;
Y is halo, trifluorophenoxy, or tetrafluorophenoxy;
$R^2$ is a $C_{1-6}$ straight chained or branched alkyl;
$R^3$ is hydrogen, halo, $OCF_3$, CN, or $CF_3$; and
$R^4$ is hydrogen, halo, $OCF_3$, SR, CN, $CF_3$, Ar, or T-Ar;
  wherein:
    T is O or S;
    R is a $C_{1-6}$ straight chained or branched alkyl;
    Ar is a phenyl ring optionally substituted with 1-3 groups selected from halo, $CH_3$, $CF_3$, CN, OMe, $OCF_3$, and $NR^5R^6$; and
    $R^5$ and $R^6$ each is independently H or $C_{1-6}$ alkyl, or $R^5$ and $R^6$, taken together, form a 5-7 membered ring optionally containing up to 3 heteroatoms selected from O, S, NH, and N($C_{1-6}$ alkyl);
provided that when Y is halo, then both, $R^3$ and $R^4$, are not simultaneously hydrogen.

The present invention also provides pharmaceutical compositions and methods using such compositions for treating a caspase-mediated disease.

DETAILED DESCRIPTION OF THE INVENTION

The present invention provides a compound of formula I:

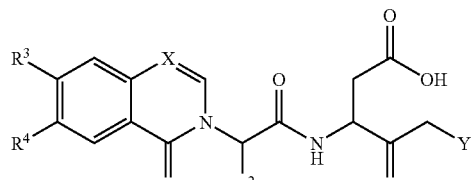

wherein:
X is CH or N;
Y is halo, trifluorophenoxy, or tetrafluorophenoxy;
$R^2$ is a $C_{1-6}$ straight chained or branched alkyl;
$R^3$ is hydrogen, halo, $OCF_3$, CN, or $CF_3$; and
$R^4$ is hydrogen, halo, $OCF_3$, SR, CN, $CF_3$, Ar, or T-Ar;
  wherein:
    T is O or S;
    R is a $C_{1-6}$ straight chained or branched alkyl;
    Ar is a phenyl ring optionally substituted with 1-3 groups selected from halo, $CH_3$, $CF_3$, CN, OMe, $OCF_3$, and $NR^5R^6$; and
    $R^5$ and $R^6$ each is independently H or $C_{1-6}$ straight chained or branched alkyl, or $R^5$ and $R^6$, taken together, form a 5-7 membered ring optionally containing up to 3 heteroatoms selected from O, S, NH, and N($C_{1-6}$-straight chained or branched alkyl);
provided that when Y is halo, then both, $R^3$ and $R^4$, are not simultaneously hydrogen.

In another embodiment of formula I, $R^4$ is hydrogen, halo, $OCF_3$, CN, $CF_3$, or T-Ar; wherein T, Ar, and the other variables are as defined above.

The compounds of the present invention represent a selection over the genus of International PCT Publication WO 01/42216, the entire disclosure of which is incorporated herein. Specifically, the compounds of the present invention have an unexpected and surprising ability to inhibit apoptosis and/or inhibit Il-1β release from activated cells.

According to a preferred embodiment, $R^2$ in formula I is ethyl, n-propyl, or isopropyl.

According to a more preferred embodiment, $R^2$ in formula I is ethyl.

According to an even more preferred embodiment, $R^2$ in formula I is (S)-ethyl.

According to a preferred embodiment, $R^3$ in formula I is hydrogen.

According to a preferred embodiment, Y in formula I is F, trifluorophenoxy, or tetrafluorophenoxy.

According to another preferred embodiment, the present invention provides a compound of formula IA:

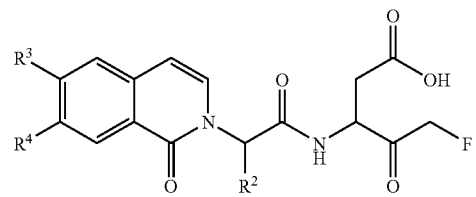

wherein:
R² is ethyl, n-propyl, or isopropyl; and
R³ and R⁴ are each independently hydrogen, halo, OCF₃, CN, CF₃, or Ar, provided that both R³ and R⁴ are not simultaneously hydrogen;
Ar is a phenyl ring optionally substituted with 1-3 groups selected from halo, CH₃, CF₃, CN, OMe, OCF₃, and NR⁵R⁶; and
R⁵ and R⁶ each is independently H or C₁₋₆ straight chained or branched alkyl, or R⁵ and R⁶, taken together, form a 5-7 membered ring optionally containing up to 3 heteroatoms selected from O, S, NH, and N(C₁₋₆-straight chained or branched alkyl);

According to another embodiment of formula IA, R³ and R⁴ are each independently hydrogen, halo, OCF₃, CN, or CF₃, provided that both, R³ and R⁴, are not simultaneously hydrogen; and R² is as defined above for formula IA.

According to a preferred embodiment, R² in the compound of formula IA is ethyl.

According to a more preferred embodiment, R² in formula IA is (S)-ethyl.

According to another preferred embodiment, R² in the compound of formula IA is isopropyl.

According to a preferred embodiment, R³ in the compound of formula IA is hydrogen.

According to a preferred embodiment, R⁴ in the compound of formula IA is F, Cl, CN, Ar, or CF₃.

According to a more preferred embodiment, R⁴ in the compound of formula IA is Cl.

According to another more preferred embodiment, R⁴ in the compound of formula IA is CF₃.

According to another preferred embodiment, R³ in the compound of formula IA is hydrogen, and R⁴ is F, Cl, CN, Ar, or CF₃.

According to another preferred embodiment, R³ in the compound of formula IA is hydrogen and R⁴ is Cl.

According to another preferred embodiment, R³ in the compound of formula IA is hydrogen and R⁴ is CF₃.

According to another preferred embodiment, R³ in the compound of formula IA is hydrogen and R⁴ is Ar.

According to another preferred embodiment, the present invention provides a compound of formula IB:

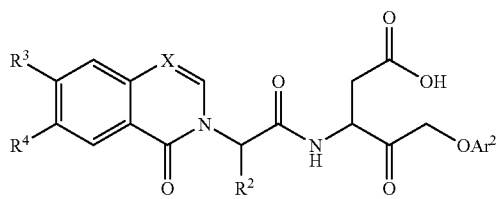

IB wherein:
X is CH or N;
R² is ethyl, n-propyl, or isopropyl;
R³ and R⁴ are each independently hydrogen, halo, OCF₃, CN, or CF₃; and
Ar is trifluorophenyl or tetrafluorophenyl.

According to a preferred embodiment, Ar² in the compound of formula IB is 2,3,5,6-tetrafluorophenyl.

According to a preferred embodiment, R² in the compound of formula IB is ethyl.

According to a more preferred embodiment, R² in formula IB is (S)-ethyl.

According to a preferred embodiment, X in the compound of formula IB is CH.

According to a preferred embodiment, R³ in the compound of formula IB is hydrogen.

According to a preferred embodiment, R⁴ in the compound of formula IB is F, Cl, or CF₃.

According to a more preferred embodiment, R⁴ in the compound of formula IB is Cl.

According to a more preferred embodiment, R⁴ in the compound of formula IB is CF₃.

According to a preferred embodiment, R³ in the compound of formula IB is hydrogen, and R⁴ is F, Cl, or CF₃.

According to another preferred embodiment, Ar² in the compound of formula IB is 2,3,5,6-tetrafluorophenyl, R³ is hydrogen, and R⁴ is Cl.

According to another preferred embodiment, the present invention provides a compound of formula IC:

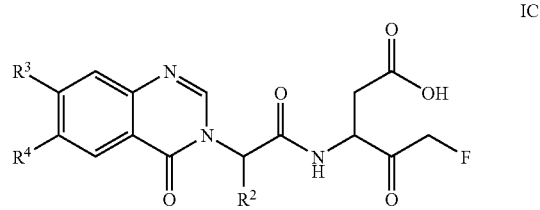

IC wherein:
R² is ethyl, n-propyl, or isopropyl;
R³ is hydrogen, halo, OCF₃, CN, or CF₃;
R⁴ is halo, OCF₃ CN, CF₃, SR, or T-Ar;
T is O or S;
R is a C₁₋₆ straight chained or branched alkyl;
Ar is a phenyl ring optionally substituted with 1-3 groups selected from halo, CH₃, CF₃, CN, OMe, OCF₃, and NR⁵R⁶; and
R⁵ and R⁶ each is independently H or C₁₋₆ straight chained or branched alkyl, or R⁵ and R⁶, taken together, form a 5-7 membered ring optionally containing up to 3 heteroatoms selected from O, S, NH, and N(C₁₋₆-straight chained or branched alkyl).

According to a preferred embodiment of the compound of formula IC, R⁴ is T-Ar;

According to a preferred embodiment, R² in the compound of formula IC is ethyl.

According to a more preferred embodiment, R² in formula IC is (S)-ethyl.

According to a preferred embodiment, $R^3$ in the compound of formula IC is hydrogen.

According to a preferred embodiment, $R^4$ in the compound of formula IC is F, Cl, CN, or $CF_3$.

According to a more preferred embodiment, $R^4$ in the compound of formula IC is Cl.

According to a preferred embodiment, T in the compound of formula IC is O.

According to a preferred embodiment, Ar if present in the compound of formula IC, is optionally substituted with $CF_3$ or halo (preferably, the halo is chloro or fluoro).

As used herein, "$C_{1-6}$" indicates the presence of 1, 2, 3, 4, 5, or 6 carbon atoms (or optional heteroatom substituted therefor).

According to a more preferred embodiment, the present invention provides a compound of formula I, selected from Table 1 below:

TABLE 1

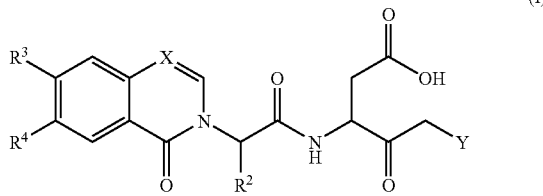

(I)

| Example | $R^4$ | $R^3$ | $R^2$ | Y | X |
|---|---|---|---|---|---|
| 1 | Cl | H | Et | F | CH |
| 2 | $CF_3$ | H | Et | F | CH |
| 3 | H | Cl | Et | F | CH |
| 4 | H | $CF_3$ | Et | F | CH |
| 5 | Cl | H | Et | 2,3,5,6-tetrafluoro-phenoxy | N |
| 6 | H | H | Et | 2,3,5,6-tetrafluoro-phenoxy | N |
| 7 | H | H | Et | 2,4,6-trifluoro-phenoxy | N |
| 8 | H | H | Et | 2,3,6-trifluoro-phenoxy | N |
| 9 | H | H | Et | 2,3,5,6-tetrafluoro-phenoxy | CH |
| 10 | Cl | H | Et | 2,3,5,6-tetrafluoro-phenoxy | CH |
| 11 | Cl | Cl | Et | 2,3,5,6-tetrafluoro-phenoxy | CH |
| 12 | 2-chloro-phenoxy | H | Et | F | N |
| 13 | 3-chloro-phenoxy | H | Et | F | N |
| 14 | 3-fluoro-phenoxy | H | Et | F | N |
| 15 | 2,4-dichloro-phenoxy | H | Et | F | N |
| 16 | phenyl-sulfanyl | H | Et | F | N |
| 17 | 3-fluoro-phenyl-sulfanyl | H | Et | F | N |
| 18 | Cl | H | i-Pr | F | CH |
| 19 | $CF_3$ | H | Et | 2,3,5,6-tetrafluoro-phenoxy | CH |
| 20 | $CF_3$ | H | Et | 2,3,5,6-tetrafluoro-phenoxy | N |
| 21 | phenyl | H | Et | F | CH |
| 22 | S(n-Pr) | H | Et | F | N |

According to another embodiment, the present invention provides a pharmaceutical composition comprising:
a) a compound of formula I, as defined above, or a pharmaceutically acceptable salt thereof; and
b) a pharmaceutically acceptable carrier, adjuvant or vehicle.

According to a preferred embodiment, the pharmaceutical composition of the present invention comprises:
a) a compound of formula IA, formula IB, or formula IC; and
b) a pharmaceutically acceptable carrier, adjuvant or vehicle.

According to a more preferred embodiment, the pharmaceutical composition of the present invention comprises a compound selected from Table 1 above.

Compounds of this invention may exist in solution as either the open form 1 or the cyclized hemiketal form 2. The representation herein of either isomeric form is meant to include the other.

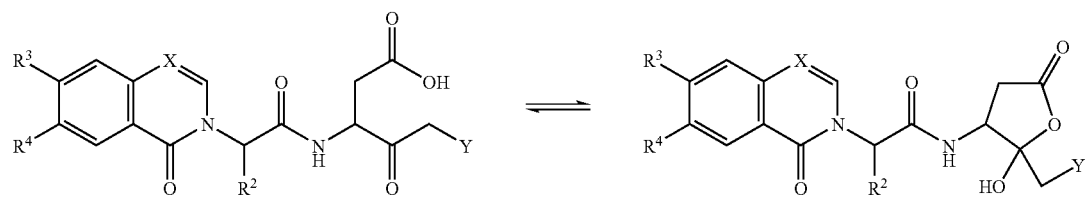

Form 1         Form 2

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

The compounds of this invention may be prepared in general by methods known to those skilled in the art for analogous compounds. Synthetic routes to the compounds of the present invention are generically described in WO 01/42216. For the purposes of illustration, the following Schemes I-IV for the synthesis of the compounds of the present invention are provided.

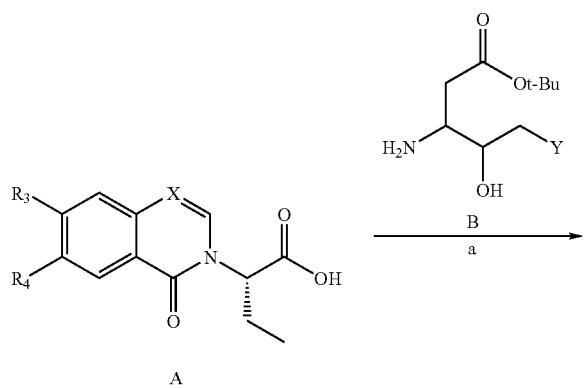

Reagents: (a) EDC/DMAP/HOBt/THF; (b) Dess-Martin periodinane; (c) TFA/DCM

In Scheme I above, the following abbreviations are used: EDC is 1-(3-dimethylaminopropyl)-3-ethylcarbodiimide; HOBt is 1-hydroxybenzotriazole; THF is tetrahydrofuran; TFA is trifluoroacetic acid; DCM is dichloromethane; DMAP is 4-dimethylaminopyridine. Acid A is coupled to amino alcohol B to give amide C. The hydroxy group in compound C is oxidized to give the ketone followed by acid hydrolysis of the tert butyl ester to give I' as the free acid.

In the case of fluoromethyl ketones where $CH_2Y$ is $CH_2F$, the amino alcohol B may be obtained according to the method of Revesz et al., *Tetrahedron Lett.* 35, 9693 (1994). In the case of fluoro-substituted phenoxy ketones where Y in $CH_2Y$ is 2,3,5,6-tetrafluorophenoxy, 2,4,6-trifluorophenoxy, or 2,3,6-trifluorophenoxy, the amino alcohol B may be obtained by methods analogous to those of Semple et al., *Bioorganic and Medicinal Chemistry Letters*, 7, 1337 (1997) (Scheme II).

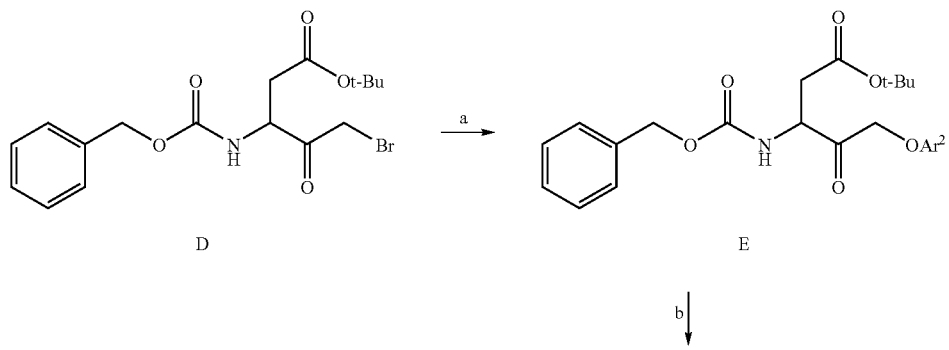

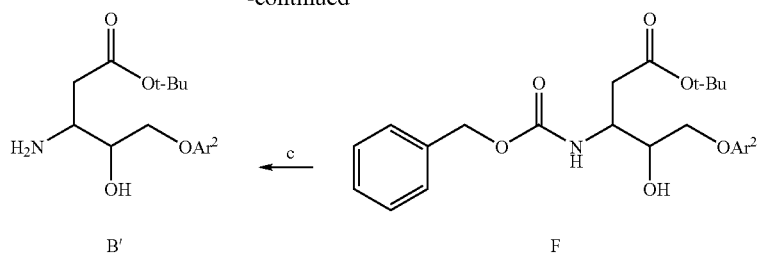

Reagents: (a) KF/DMF/Ar²OH; (b) NaBH₄/THF; (c) H₂/Pd/C/MeOH

In scheme II above, the following abbreviations are used: KF is potassium fluoride; DMF is N,N-dimethylformamide; Ar²OH is either 2,3,5,6-tetrafluorophenol, 2,4,6-trifluorophenol or 2,3,6-trifluorophenol; THF is tetrahydrofuran; MeOH is methanol. Commercially available bromoketone D is reacted with the appropriately substituted fluorophenol and potassium fluoride to give phenoxy ketone E. The ketone is then reduced with sodium borohydride to give the alcohol F, which is hydrogenated using palladium on carbon as catalyst to give the amino alcohol B' (Ar²=fluoro-substituted phenyl).

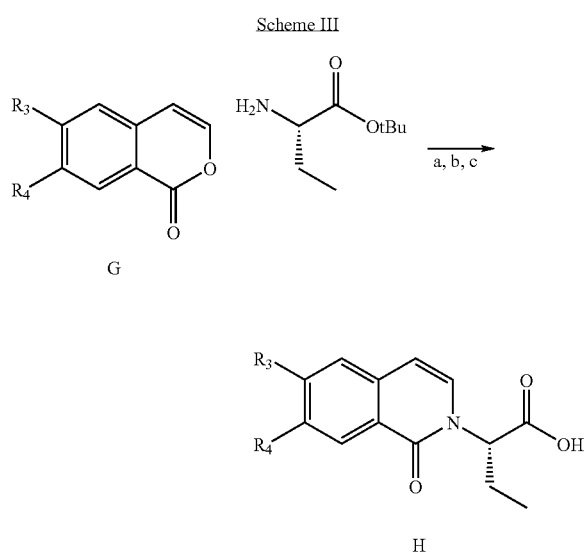

Reagents: (a) heat; (b) conc. HCl/IPA; (c) TFA/DCM

In Scheme III above, the following abbreviations are used: IPA is isopropyl alcohol; TFA is trifluoroacetic acid and DCM is dichloromethane. Isoquinolin-1-one acid derivatives (in formula I, X=C) can be prepared in chiral form using the synthetic sequence shown in Scheme III. The starting isocoumarin G is prepared by methods analogous to Narasimhan et al., *Synthesis*, 797 (1975) and Margaretha et al., *Tetrahedron* 56, 6763 (2000) unless stated otherwise. Isocoumarin G is first heated with commercially available (S)-2-aminobutyric acid, tert-butyl ester. The resulting compound is reacted with concentrated hydrochloric acid in isopropanol to give the isoquinolin-1-one tert-butyl ester which is deprotected to provide the acid H using trifluoroacetic acid. The acid is then coupled to amino alcohol B (Scheme I).

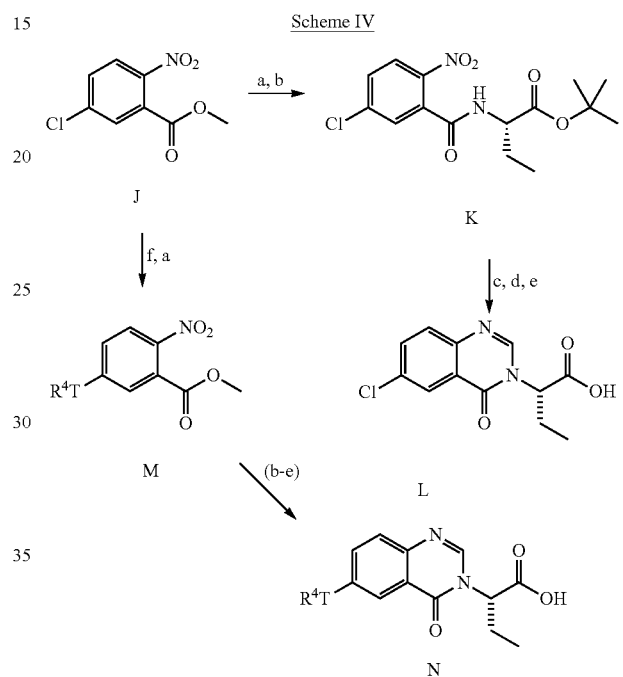

Reagents: (a) LiOH/THF/H₂O; (b) (S)-2-Aminobutyric acid, tert-butyl ester/EDC/HOBt/DMAP/THF; (c) SnCl₂/MeOH; (d) Trimethylorthoformate/AcOH/reflux; (e) TFA/DCM; (f) R⁴-TH/K₂CO₃/DMF.

In scheme IV above, the following abbreviations are used: AcOH is acetic acid and R⁴-TH can be 2-chlorophenol, 3-chlorophenol, 3-fluorophenol or 2,4-dichlorophenol or thiophenol or 3-fluorothiophenol. (4-oxo-4H-quinazolin-3-yl) acid derivatives A (X=N) are prepared in chiral form using methods analogous to Makino et al., *Synlett*, 11, 1670 (2000). Commercially available 5-chloro-2-nitrobenzoic acid methyl ester J is hydrolysed to the acid using lithium hydroxide and the resulting acid coupled to commercially available (S)-2-aminobutyric acid tert-butyl ester to give amide K. Reduction of the nitro group using tin (II) chloride followed by acid catalysed cyclo-condensation with trimethylorthoformate furnishes the quinazoline, which is deprotected with trifluoroacetic acid to give the 4-oxo-4H-quinazolin-3-yl acid L. The acid is then coupled to the amino alcohol B (Scheme I). Alternatively, 5-chloro-2-nitrobenzoic acid methyl ester J can be reacted with a suitably substituted phenol or thiophenol by heating with potassium carbonate in DMF to give the corresponding 6-phenoxy (Y=O) or 6-phenylsulfanyl (Y=S) derivative. Treatment with lithium hydroxide gives the acid M, which can be further elaborated (Scheme IV, steps b-e) to give 4-oxo-4H-quinazolin-3-yl acid N which is then coupled to amino alcohol B as previously described. 2-Nitrobenzoic acid may also be elaborated in an analogous manner to furnish the unsubstituted 4-oxo-4H-quinazolin-3-yl acid.

Accordingly one aspect of this invention relates to a general method of preparing a compound of formula I, comprising the steps of:

reacting an acid or acid derivative of formula II,

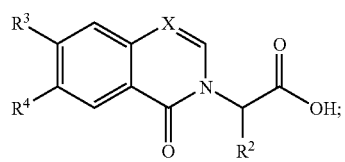

II with an amino alcohol of formula B to provide a compound of formula III,

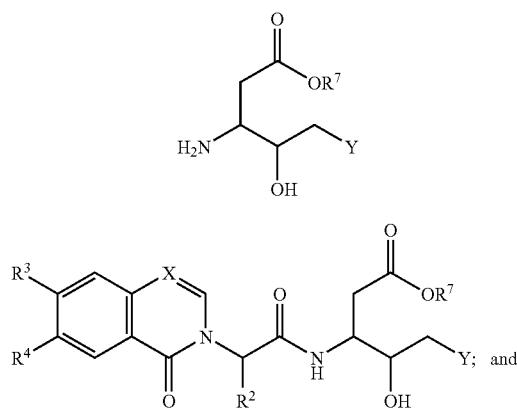

B

III converting intermediate III to compound I, wherein; $R^7$ is a suitable protecting group, and Y, X, $R^2$, $R^3$, and $R^4$ are as described in any of the embodiments herein. A suitable protecting group would be known to skilled practitioners (see e.g., "Protective Groups in Organic Synthesis" Third Ed. Greene, T. W. and Wuts, P. G., Eds., John Wiley & Sons, New York: 1999, the entire contents of which is hereby incorporated by reference). Preferably $R^7$ is a $C_{1-6}$ straight or branched alkyl. More preferably, $R^7$ is t-butyl.

The compound of formula II and the compound of formula B may be reacted under any conditions for coupling an amino compound and an acid compound. Such conditions are well known to skilled practitioners. Preferred coupling conditions are those described in the schemes and examples herein.

The compound of formula III may be converted to a compound of formula I under any conditions for converting a hydroxy group to a carbonyl group and converting a protected acid to the free acid. Such conditions are well known to skilled practitioners. Preferred conditions for preparing a carbonyl group from a hydroxyl group are those oxidizing conditions described in the schemes and examples herein. Preferred conditions for deprotecting a protected acid when $R^7$ is t-butyl are those hydrolysis conditions described in the schemes and examples herein.

This method is particularly useful for preparing chiral compounds of this invention, where the carbon bearing the $R^2$ substituent is stereochemically enriched. As exemplified below (see e.g., Examples 1-22), intermediate acids or acid derivatives of formula II may be obtained in chiral form. This is illustrated herein for quinazolin-4-ones where X is nitrogen (see e.g., Examples 5-8, 12-18, 20, and 22) and for isoquinolin-1-ones where X is CH (see e.g., Examples 1-4, 9-11, 19, and 21). The coupling of II and B to provide III may be carried out according to any suitable method. The conversion of III to provide I may be performed as described herein or according to other methods familiar to those skilled in the art.

Certain chiral intermediates of II are useful in processes for preparing compounds of this invention. A preferred intermediate is represented by compound IIA:

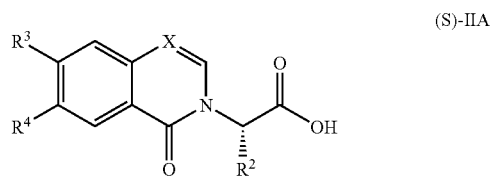

(S)-IIA wherein X, $R^2$, $R^3$, and $R^4$ are as described in any of the embodiments herein.

According to a more preferred embodiment for compounds of formula II and IIA, $R^2$ is ethyl or isopropyl.

The compounds of this invention can be assayed for their ability to inhibit apoptosis, the release of IL-1β or caspase activity directly. Assays for each of the activities are known in the art and are described below in detail in Examples 23-25.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents, which are commonly, used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers, which are commonly used, include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemia's and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polycystic kidney disease, *H. pylori*-associated gastric and duodenal ulcer disease, HIV infection, tuberculosis, an immunotherapy for the treatment of various forms of cancer, organ failure, and meningitis. The compounds and compositions are also useful in treating complications associated with coronary artery bypass grafts. The amount of compound present in the above-described compositions should be sufficient to cause a detectable decrease in the severity of the disease or in caspase activity and/or cell apoptosis, as measured by any of the assays known in the art.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention. Both the compound and the additional agent should be present at dosage levels of between 10 to 100%, and more preferably between about 10 to 80% of the dosage normally administered in a monotherapy regimen.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting caspase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of caspase activity in a biological sample is useful for a variety of purposes that are known to one of skill in the art. Examples of such purposes include, but are not limited to, blood transfusion, organ-transplantation, biological specimen storage, and biological assays.

The compounds of this invention are useful in methods for preserving cells, such as may be needed for an organ transplant or for preserving blood products. Similar uses for caspase inhibitors have been reported (Schierle et al., *Nature Medicine*, 5, 97 (1999)). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

In order that this invention be more fully understood, the following preparative and testing examples are set forth. These examples are for the purpose of illustration only and are not to be construed as limiting the scope of the invention in any way.

EXAMPLE 1

(S)-3-[2-(7-chloro-1-oxo-1H-isoquinolin-2-yl)-butyrylamino]-5-fluoro-4-oxo-pentanoic acid

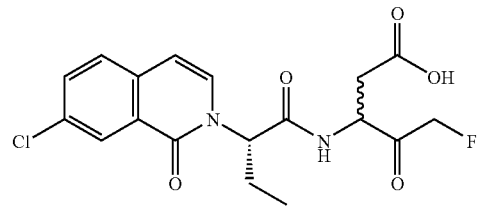

Method A:

5-Chloro-2(2-methoxyvinyl)-benzoic acid

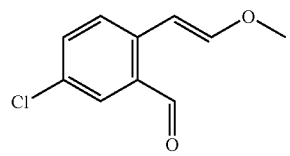

To a cooled (0° C.) slurry of methoxymethyltriphenylphosphonium chloride (39 g) in a mixture of diethyl ether (200 ml) and tert-butanol (50 ml) was added potassium tert-butoxide (12.8 g) portion wise. The resulting mixture was stirred at 0° C. for 1 hour, then a solution of 2-formyl-5-chlorobenzoic acid (prepared as described in *J. Org. Chem.* 61, 3402 (1996)) (10 g) in diethyl ether (50 ml) was added dropwise over 15 minutes. The resulting mixture was stirred for 1 hour at 0° C., then warmed to ambient and stirred for an additional 90 minutes. The mixture was diluted with water (200 ml) and the organic phase removed. The aqueous phase was acidified to pH 1 with 1M HCl and extracted with ethyl acetate (3×50 ml). The combined extracts were washed with brine, dried (magnesium sulfate), filtered and concentrated. The residue was purified by flash chromatography (50% ethyl acetate/hexane) to afford the sub-title compound as a yellow solid (9.13 g, 80%). $^1$H NMR (400 MHz, CDCl$_3$) δ 3.70-3.81 (3H, s), 6.20 (0.3H, d, cis alkene), 6.30 (0.3H, d, cis alkene), 6.80 (0.7H, d, trans alkene), 7.01 (0.7H, d, trans alkene), 7.30-8.15 (3H, m) ppm.

Method B:

7-Chloro-isochromen-1-one

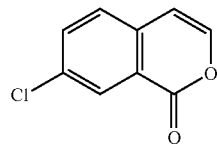

Concentrated sulphuric acid (15 ml) was added to 5-chloro-2(2-methoxyvinyl)-benzoic acid (4.43 g) at 0° C. The mixture was stirred for 2 hours, then diluted with ice/water. The product was extracted with ethyl acetate (3×15 ml) and the combined extracts washed with saturated sodium bicarbonate solution. The solution was dried (magnesium sulfate), filtered and concentrated. The residue was purified by flash chromatography (0-5% ethyl acetate/hexane) to afford the sub-title compound as a white solid (3.04 g, 81%). mp 109.8-110.9° C. $^1$H NMR (400 MHz, CDCl$_3$) δ 6.51 (1H, d), 7.28-7.32 (1H, m), 7.41 (1H, d), 7.64-7.70 (1H, m), 8.28 (1H, m) ppm.

Method C:

(S)-2-[3-(1-tertButoxycarbonyl-propylamino)-7-chloro-1-oxo-3,4-dihydro-1H-isoquinolin-2-yl]-butyric acid tert-butyl ester

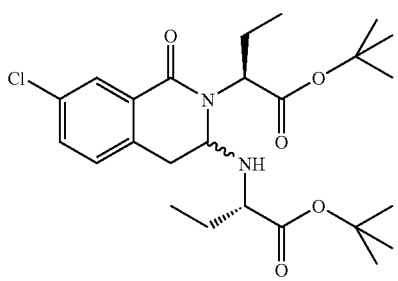

A mixture of 7-chloro-isochromen-1-one (10 g) and (S)-2-aminobutyric acid, tert butyl ester (22 g) were heated at 85° C. for 24 hours. The mixture was then cooled and purified by flash chromatography (5-25% ethyl acetate/hexane) to afford the sub-title compound as a yellow oil (17.1 g, 64%). $^1$H NMR (400 MHz, CDCl$_3$) δ 0.68-1.32 (6H, m), 1.50 (21H, m), 1.92 (1H, m), 2.15 (1H, m), 2.82-3.40 (3H, m), 4.41 (1H, m), 4.68 (1H, m), 7.11 (1H, m), 7.35-7.52 (1H, m), 8.05 (1H, m) ppm.

Method D:

(S)-2-(7-Chloro-1-oxo-1H-isoquinolin-2-yl)-butyric acid, tert butyl ester

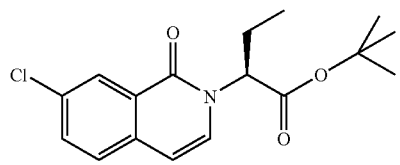

To a stirred solution of 2-[3-(1-tertbutoxycarbonyl-propylamino)-7-chloro-1-oxo-3,4-dihydro-1H-isoquinolin-2-yl]-butyric acid tert-butyl ester (8.58 g) in isopropanol (180 ml) at 0° C. was added concentrated hydrochloric acid (20 ml). The resulting mixture was allowed to warm to room temperature and stirred for 18 hours. The mixture was then diluted with ethyl acetate (500 ml) and water (150 ml). The organic phase was separated and washed with water, then brine, dried (magnesium sulfate), filtered and concentrated. The sub-title product was obtained as a yellow solid (5.57 g, 97%). m.p. 111.3-111.8° C.; [α]$^{25}_D$ −52.3° (c=1, CHCl$_3$); IR (solid) 1731.4, 1649.5, 1593.2, 1229.6, 1152.8, 901.9 cm$^{-1}$; $^1$H NMR (400 MHz, CDCl$_3$) δ 0.95 (3H, t), 1.48 (9H, s), 1.95 (1H, m), 2.30 (1H, m), 5.55 (1H, m), 6.40 (1H, m), 7.15 (1H, m), 7.49 (1H, m), 7.61 (1H, m), 8.40 (1H, m) ppm; $^{13}$C NMR (100 MHz, CDCl$_3$) δ 10.9, 24,8, 28.1, 59.2, 82,8, 105.7, 127.3, 127.8, 128.1, 129.5, 133.1, 133.2, 135.4, 161.8, 170.2; MS ES(+) 322.4 (M+H).

Method E:

(S)-2-(7-Chloro-1-oxo-1H-isoquinolin-2-yl)-butyric acid

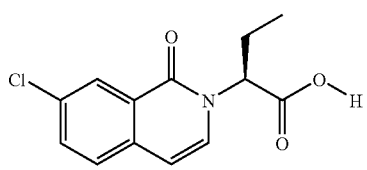

A solution of (S)-2-(7-chloro-1-oxo-1H-isoquinolin-2-yl)-butyric acid, tert-butyl ester (322 mg) in dichloromethane (14 ml) was cooled to 0° C. Trifluoroacetic acid (3.5 ml) was added and the resulting mixture allowed to warm to room temperature and stirred for 2 hours. The mixture was then concentrated under reduced pressure and the residue re-dissolved in dichloromethane. This process was repeated several times in order to remove excess trifluoroacetic acid. The resulting solid was slurried in diethyl ether, filtered and washed with more diethyl ether. The solid was then dried to constant weight under vacuum. This gave the sub-title product as a white solid (236 mg, 89%). m.p. 159.6-160.1° C.; [α]$^{24}_D$ −47.0° (c=1.01, CHCl$_3$); IR (solid) 1731.4, 1639.3, 1577.8, 1209.1, 1168.1 cm$^{-1}$; $^1$H NMR (400 MHz, d$_6$-DMSO) δ 0.82 (3H, t), 2.00-2.25 (2H, m), 5.20 (1H, m), 6.70 (1H, d), 7.49 (1H, d), 7.70-7.81 (2H, m), 8.18 (1H, s) ppm; $^{13}$C NMR (100 MHz, d$_6$-DMSO) δ 10.8, 22.7, 60.8, 104.9, 126.5, 126.6, 128.8, 131.6, 132.5, 133.1, 135.8, 160.5, 171.7; MS ES (+) 266.27 (M+H).

Method F:

(S)-3-[2-(7-Chloro-1-oxo-1H-isoquin-2-yl)-butyrylamino]-5-fluoro-4-hydroxy-pentanoic acid tert-butyl ester

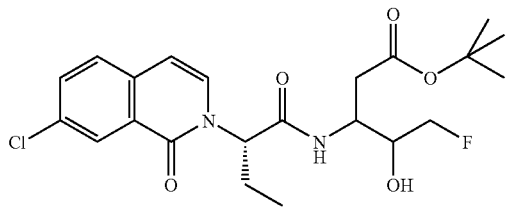

A stirred mixture of (S)-2-(7-chloro-1-oxo-1H-isoquinolin-2-yl)-butyric acid (15 g), 3-amino-5-fluoro-4-hydroxy-pentanoic acid tert-butyl ester (prepared as described in *Tetrahedron Lett.* 35, 9693 (1994)) (12.9 g), HOBt (8.4 g), DMAP (7.2 g) and THF (450 ml) was cooled to 0° C. then EDC (11.9 g) was added. The mixture was allowed to warm to room temperature during 16 h then concentrated under reduced pressure. The residue was purified by flash chromatography (30-60% ethyl acetate/hexane) to afford the subtitle compound as a white foam (24.6 g, 96%). $^1$H NMR (400 MHz, CDCl$_3$) δ 0.92 (3H, m), 1.13-1.50 (9H, m), 1.95 (1H, m), 2.25 (1H, m), 2.45-2.78 (2H, m), 3.68-4.60 (5H, m), 5.50 (1H, m), 6.60 (1H, m), 7.21-7.60 (4H, m), 8.20-8.31 (1H, m) ppm; $^{19}$F NMR (376 MHz, CDCl$_3$) (proton decoupled) δ −229.6, −229.7, −230.5, −230.6.

Method G:

(S)-3-[2-(7-Chloro-1-oxo-1H-isoquin-2-yl)-butyrylamino]-5-fluoro-4-oxo-pentanoic acid tert-butyl ester

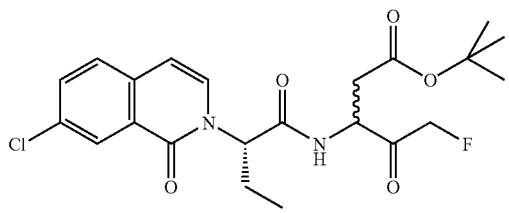

A stirred solution of 3-[2-(7-chloro-1-oxo-1H-isoquin-2-yl)-butyrylamino]-5-fluoro-4-hydroxy-pentanoic acid tert-butyl ester (47.8 g) in anhydrous DCM (1.2 L) was treated with 1,1,1-triacetoxy-1,1-dihydro-1,2-benziodoxol-3(1H)-one (53.5 g) at 0° C. The resulting mixture was kept at 0° C. for 2 hrs., diluted with ethyl acetate, then poured into a 1:1 mixture of saturated aqueous sodium hydrogen carbonate and saturated aqueous sodium thiosulfate. The organic layer was removed and the aqueous layer re-extracted with ethyl acetate. The combined organic extracts were dried (magnesium sulfate), filtered and concentrated. The residue was purified by flash chromatography (20-40% ethyl acetate/hexane) to afford the subtitle compound as a white solid (41.9 g, 88%). $^1$H NMR (400 MHz, CDCl$_3$) δ 1.00 (3H, t), 1.29 (5H, s), 1.41 (4H, s), 2.01 (1H, m), 2.29 (1H, m), 2.61-3.05 (2H, m), 4.77 (3H, m), 5.50 (1H, m), 6.60 (1H, m), 7.20-7.34 (2H, m), 7.51 (1H, m), 7.62 (1H, m), 8.41 (1H, m) ppm; $^{19}$F NMR (376 MHz, CDCl$_3$) (proton decoupled) δ −231.89, −232.30.

(S)-3-[2-(7-chloro-1-oxo-1H-isoquinolin-2-yl)-butyrylamino]-5-fluoro-4-oxo-pentanoic acid

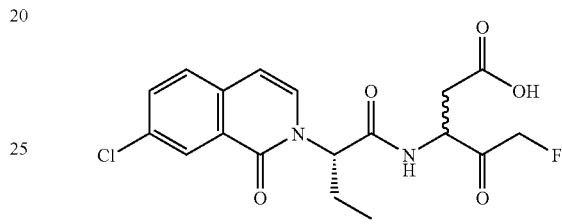

This was prepared using a procedure similar to that described in method E. The product was isolated as a white solid (98%). IR (solid) 1782.7, 1741.7, 1644.4, 1593.2, 1536.8, 1209.1, 1168.1, 1055.5, 840.4 cm$^{-1}$; $^1$H NMR (400 MHz, d$_6$-DMSO) δ 0.82 (3H, m), 1.81-2.25 (2H, m), 2.25-3.11 (2H, m), 4.15-5.60 (4H, m), 6.70 (1H, m), 7.55 (1H, m), 7.78 (2H, m), 8.15 (1H, s), 8.35-9.00 (1H, brm) ppm; $^{13}$C NMR (100 MHz, d$_6$-DMSO) δ 10.6, 23.0, 24.0, 24.6, 32.9, 34.6, 34.7, 47.7, 52.2, 52.3, 58.2, 58.23, 58.7, 59.1, 83.4, 83.5, 85.2, 85.3, 103.9, 104.5, 104.7, 104.8, 126.5, 126.6, 128.8, 131.3, 131.4, 131., 133.1, 135.7, 135.73, 160.8, 170.2, 170.3, 170.4, 172.0, 173.1, 202.6, 202.7; $^{19}$F NMR (376 MHz, d$_6$-DMSO) (proton decoupled) δ −226.70, −226.75, −227.51, −230.5, −231.16, −232.61, −232.67, −233.37; MS ES (−) 395.33 (M−H).

EXAMPLE 2

(S)-3-[2-(7-trifluoromethyl-1-oxo-1H-isoquinolin-2-yl)-butyrylamino]-5-fluoro-4-oxo-pentanoic acid

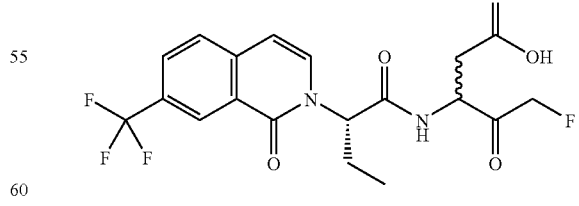

This was prepared using procedures similar to those described in methods A-G (2-formyl-5-trifluoromethylbenzoic acid was prepared using a procedure similar to that described in *J. Org. Chem.* 61, 3402 (1996). The product was isolated as a white solid (93% last step). IR (solid) 1782.6, 1746.8, 1644.4, 1629.0, 1603.4, 1321.8, 1275.7, 1168.1, 1127.2, 927.5 cm$^{-1}$; $^1$H NMR (400 MHz, d$_6$-DMSO) δ 0.82 (3H, m), 1.85-2.21 (2H, m), 2.35-3.21 (2H, m), 4.20-5.75 (4H, m), 6.80 (1H, m), 7.68 (1H, m), 7.92 (1H, m), 8.04 (1H, m), 8.49 (1H, s), 8.56-8.95 (1H, brm) ppm; $^{19}$F NMR (376 MHz, d$_6$-DMSO) (proton decoupled) δ -61.32, -61.38, -226.70, -226.76, -230.47, -231.06, -232.61, -232.67; MS ES (-) 429.30 (M-H).

EXAMPLE 3

(S)-3-[2-(6-chloro-1-oxo-1H-isoquinolin-2-yl)-butyrylamino]-5-fluoro-4-oxo-pentanoic acid

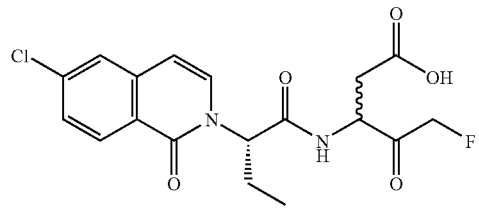

Method H:

4-Chloro-N-methyl-benzamide

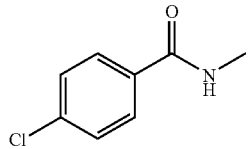

To a 0° C. solution of the 4-chlorobenzoyl chloride (4.50 g) in dichloromethane (10 mL) was added an 8M solution of methylamine in ethanol dropwise. The solution was stirred for 16 h and then evaporated to dryness. The residue was diluted with saturated sodium bicarbonate solution (10 mL) and extracted three times with ethyl acetate (3×20 mL), the organics washed with brine (10 mL), dried (MgSO$_4$) and concentrated in vacuo to afford the sub-title compound as a white solid (4.33 g; 97%). $^1$H NMR (400 MHz, CDCl$_3$) δ 3.00 (3H, s), 7.40 (1H, br) 7.40 (1H, d), 7.70 (1H, d) ppm.

Method I:

2-formyl-4-chloro-N-methylbenzamide

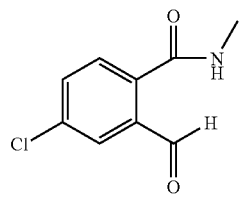

To a solution of 4-chloro-N-methyl-benzamide (3.1 g) in THF (30 mL) was added n-butyl lithium (30.1 mL of 2.5M hexane solution) and the solution refluxed for 45 min. The solution was then cooled to 0° C. and N-methylformanilide (9.27 mL) added dropwise over 2 min. The solution was then refluxed for 2 h, then cooled to ambient temperature, water (80 mL) added and the solution acidified to pH 1 with 2M HCl. The solution was then extracted three times with ethyl acetate (3×50 mL), washed with brine (20 mL), dried (MgSO$_4$) and concentrated in vacuo. The resulting brown oil was purified on silica by flash chromatography to afford the sub-titled product as a pale yellow solid (2.13 g; 59%). $^1$H NMR (400 MHz, CDCl$_3$) δ 2.90 (3H, s), 4.25 (1H, d, J) 5.60 (1H, d, J), 7.35 (2H, s), 7.60 (1H, s) ppm.

Method J

2-Formyl-4-chlorobenzoic acid

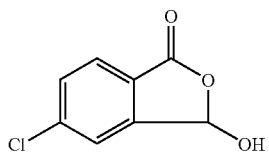

A mixture of 2-formyl-4-chloro-N-methylbenzamide (3.19 g) and 10M hydrochloric acid (30 ml) was heated at reflux for 18 hours. The mixture was cooled and basified with saturated sodium hydrogen carbonate solution. The solution was then washed with ethyl acetate, then acidified with 2M hydrochloric acid. The product was extracted with ethyl acetate and the combined extracts dried with magnesium sulfate. The solution was then filtered and concentrated. This furnished 2-formyl-4-chlorobenzoic acid as a yellow solid (2.22 g, 75%). $^1$H NMR (400 MHz, CDCl$_3$) δ 6.65 (0.5H, brs), 7.50 (2H, m), 7.65 (1H, m), 7.85 (0.5H, brm), 8.05 (1H, m) ppm.

(S)-3-[2-(6-chloro-1-oxo-1H-isoquinolin-2-yl)-butyrylamino]-5-fluoro-4-oxo-pentanoic acid

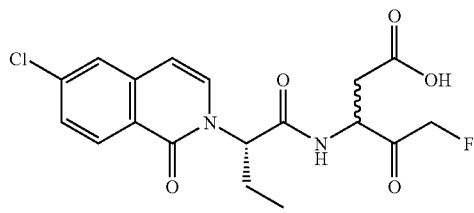

This was prepared from 2-formyl-4-chlorobenzoic acid (prepared as described in methods H-J) using procedures similar to those described in methods A-G. The title compound was isolated by preparative HPLC and was obtained as a white solid. $^1$H NMR (400 MHz, CDCl$_3$) δ 0.97 (3H, m), 1.90-2.31 (2H, m), 2.65-3.30 (2H, m), 4.20-5.75 (4H, m), 6.65 (1H, m), 7.40-7.60 (3H, m), 8.29 (1H, m), 9.20 (1H, br) ppm; $^{19}$F NMR (376 MHz, CDCl$_3$) (proton decoupled) δ -229.80, -232.07, -232.43, -232.58, -232.78; MS ES (-) 395.26 (M-H).

EXAMPLE 4

(S)-3-[2-(6-trifluoromethyl-1-oxo-1H-isoquinolin-2-yl)-butyrylamino]-5-fluoro-4-oxo-pentanoic acid

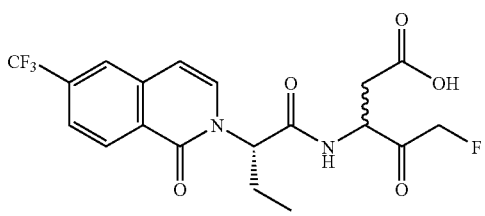

This was prepared from 2-formyl-4-trifluoromethylbenzoic acid (prepared from 4-trifluoromethylbenzoic acid using methods similar to those described in H-J) using procedures similar to those described in methods A-G. The title compound was isolated as a white solid (95%, last step). $^1$H NMR (400 MHz, CDCl$_3$) δ 0.99 (3H, m), 1.90-2.30 (2H, m), 2.60-3.50 (2H, m), 4.20-5.75 (4H, m), 6.80 (1H, m), 7.50-7.90 (3H, m), 7.92 (1H, m), 8.40-8.60 (1H, m) ppm; $^{19}$F NMR (376 MHz, d$_6$-DMSO) (proton decoupled) δ −63.60, −63.61, −63.65, −231.67, −231.80, −232.06, −232.18; MS ES(+) 431.26 (M+H).

EXAMPLE 5

(S,S)-3-[2-(6-Chloro-4-oxo-4H-quinazolin-3-yl)-butyrylamino]-4-oxo-5-(2,3,5,6-tetrafluoro-phenoxy) pentanoic acid

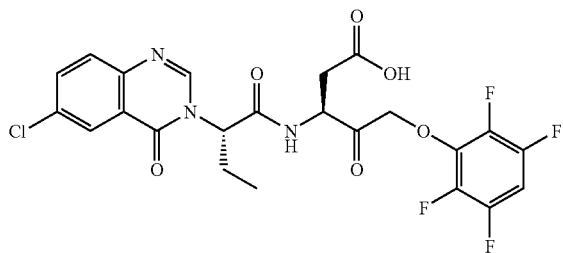

Method K:

(S)-2-(5-chloro-2-nitro-benzoylamino)-butyric acid-tert-butyl ester

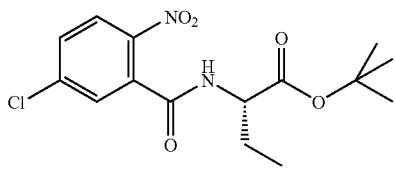

To a stirred solution of 5-chloro-2-nitro-benzoic acid (4.68 g) in anhydrous tetrahydrofuran (100 ml) at 0° C., was added (S)-2-amino-butyric acid-tert-butyl ester hydrochloric acid salt (5 g), HOBt (3.45 g), DMAP (2.98 g), followed by EDC (4.88 g) and diisopropylethylamine (3.30 g). The reaction mixture was stirred for 10 minutes then warmed to room temperature and stirred for 16 hours before concentration at reduced pressure. The resulting residue was partitioned between EtOAc (100 ml) and saturated sodium bicarbonate solution (100 ml), the organic layer separated and further washed with 1M hydrochloric acid and saturated brine solution, dried (MgSO4), filtered and concentrated to give the sub-title compound as a pale yellow oil (6.82 g, 68% yield). $^1$H NMR (400 MHz, CDCl$_3$) δ 8.05 (1H, d), 7.55 (2H, m), 6.4 (1H, m) 4.7 (1H, m), 2.1 (1H, m), 1.95 (1H, m), 1.5 (9H, s), 1.0 (3H, t) ppm.

Method L:

(S)-2-(2-amino-5-chloro-benzoylamino)-butyric acid-tert-butyl ester

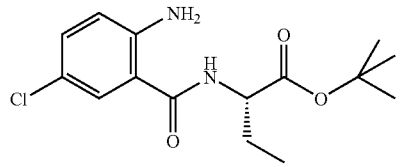

To a stirred solution of (S)-2-(5-chloro-2-nitro-benzoylamino)-butyric acid-tert-butyl ester (5.72 g,) in ethanol (250 ml) at ambient temperature was added tin(II) chloride bishydrate (18.8 g). The mixture was stirred at ambient for 16 hours. The volume was reduced to approximately 50 ml under reduced pressure, and reaction mixture was then diluted with 1M NaOH until the precipitate formed re-dissolved (400 ml). The aqueous was then extracted with diethyl ether (3×100 ml). The organic extracts were combined and washed with brine, dried (MgSO$_4$), and concentrated to give the sub-titled compound as a yellow solid (4.60 g, 88% yield). $^1$H NMR (400 MHz, CDCl$_3$) δ 7.4 (1H, s), 7.2 (1H, d), 6.6 (2H, m), 5.5 (2H, m), 4.6 (1H, m), 2.0 (1H, m), 1.85 (1H, m), 1.5 (9H, s), 0.95 (3H, t) ppm.

Method M:

(S)-2-(6-chloro-4-oxo-4H-quinazoline-3-yl)-butyric acid-tert-butyl ester

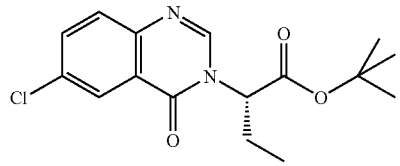

2-(2-amino-5-chloro-benzoylamino)-butyric acid-tert-butyl ester (2.82 g) was dissolved in trimethylorthoformate (50 ml). Acetic acid (10 ml) was added, and reaction mixture refluxed for 48 hours. After this time, the solvents were removed and the residue partitioned between ethyl acetate and saturated sodium bicarbonate solution. The aqueous layer was further extracted with ethyl acetate and the combined organic extracts washed with brine, dried (MgSO$_4$) and concentrated under reduced pressure to give a yellow oil. This was purified by flash chromatography (20% EtOAc: Petroleum) to give the sub-title compound as an oil (1.23 g, 42% yield). $^1$H NMR (400 MHz, CDCl$_3$) δ 8.25 (1H, s), 8.05 (1H, s), 7.7 (2H, m), 5.3 (1H, m), 2.3 (1H, m), 2.0 (1H, m), 1.5 (9H, s), 1.0 (3H, t) ppm.

2-(6-chloro-4-oxo-4H-quinazoline-3-yl)-c acid

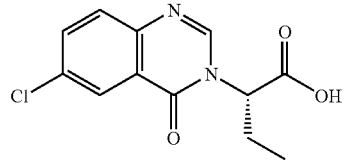

This was prepared using a procedure similar to that described in method E. The sub-title compound was obtained as an off-white solid. $^1$H NMR (400 MHz, MeOD) δ 8.3 (1H, s), 8.15 (1H, s), 7.8 (1H, d), 7.7 (1H, d), 5.2 (1H, m), 2.4 (1H, m), 2.2 (1H, m), 0.95 (3H, t) ppm.

Method N:

(S)-3-Benzyloxycarbonylamino-4-oxo-5-(2,3,5,6-tetrafluoro-phenoxy)-pentanoic acid tert-butyl ester

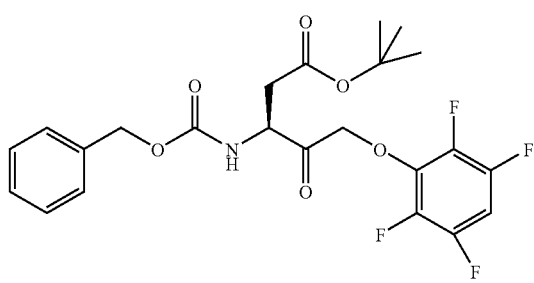

Potassium fluoride (2.8 g) was added portionwise to a stirred solution of (S)-3-benzyloxycarbonylamino-5-bromo-4-oxo-pentanoic acid tert-butyl ester (18.6 g) and 2,3,5,6-tetrafluorophenol (9.3 g) in anhydrous DMF (250 mL) under nitrogen at room temperature. The mixture was then stirred for 18 hours before being quenched with ethyl acetate and water. The organic layer was removed and washed with sodium bicarbonate solution, dried (magnesium sulfate) and concentrated to give the sub-title product as an off-white solid (21.1 g, 96%). $^1$H NMR (400 MHz, CDCl$_3$) δ 1.43 (9H, s), 2.76 (1H, dd), 3.06 (1H, dd), 4.67-4.71 (1H, m), 5.12 (1 h, d), 5.22 (1H, d), 5.86 (1H, d), 7.35-7.38 (5H, m) ppm; $^{19}$F NMR (376 MHz, CDCl$_3$) (proton decoupled) δ −139.98, −140.00, −140.04, −140.06, −157.05, −157.07, −157.11, −157.13; MS ES (+) 486.23 (M+H).

Method O:

(3S)-3-Benzyloxycarbonylamino-4-hydroxy-5-(2,3,5,6-tetrafluoro-phenoxy)-pentanoic acid tert-butyl ester

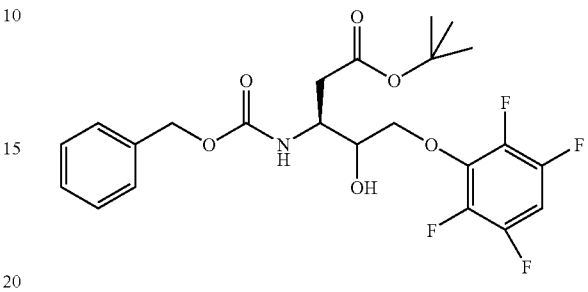

NaBH$_4$ (1.65 g) was added portionwise to a stirred solution of 3-benzyloxycarbonylamino-4-oxo-5-(2,3,5,6-tetrafluoro-phenoxy)-pentanoic acid tert-butyl ester (21.1 g) in anhydrous THF (220 mL) at −20° C. under nitrogen. After stirring at this temperature for 3 hours, the reaction was quenched by the addition of saturated ammonium chloride solution and diluted with DCM. The organic layer was removed and the aqueous layer re-extracted with DCM. The combined organic extracts were washed with brine, dried (magnesium sulfate) and concentrated. The residue was purified by column chromatography (10%-20% ethyl acetate/hexane). The sub-title compound was obtained as a white solid (14.6 g, 73%). $^1$H NMR (400 MHz, CDCl$_3$) δ 1.45 (9H, s), 2.61-2.77 (2H, m), 3.16-3.36 (1H, 2×brd d), 4.12-4.22 (2H, m), 4.30-4.33 (1H, m), 5.44-5.69 (1H, 2×d), 6.78-6.86 (1H, m), 7.35-7.36 (5H, m) ppm; $^{19}$F NMR (346 MHz, CDCl$_3$) (proton decoupled) δ −139.87, −139.89, −139.93, −139.95, −139.98, −157.02, −157.05, −157.06, −157.08, −157.09, −157.10, −157.12; ES (+) 488.27 (M+H).

Method P:

(3S)-3-Amino-4-hydroxy-5-(2,3,5,6-tetrafluoro-phenoxy)-pentanoic acid tert-butyl ester

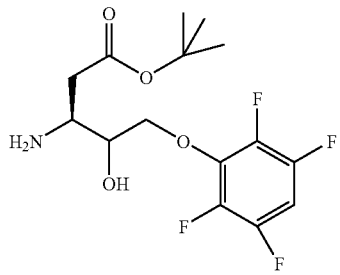

10% Pd on carbon (2.92 g) was added portionwise to a solution of 3-benzyloxycarbonylamino-4-hydroxy-5-(2,3,5,6-tetrafluoro-phenoxy)-pentanoic acid tert-butyl ester (14.6 g) in anhydrous MeOH (350 mL) which had been degassed under nitrogen (5×). The reaction was further degassed under nitrogen (3×) and hydrogen (5×) and stirred at room temperature for 20 minutes. The palladium catalyst was removed by filtration and the filtrate concentrated to give the sub-titled compound as a white solid (9.5 g, 90%). $^1$H NMR (400 MHz, CDCl$_3$) δ 1.49 (9H, s), 2.35-2.43 (1H, m), 5.67-5.64 (1H, m), 3.37-3.43 (1H, m), 3.77-3.87 (1H, m), 4.28-4.63 (2H, m), 6.77-6.86 (1H, m) ppm; $^{19}$F NMR (346 MHz, CDCl$_3$) (proton decoupled) δ −139.95, −139.97, −140.00, −140.03, −140.05, −140.08, −140.11, −140.13, −157.15, −157.18, −157.21, −157.23, −157.27, −157.29.

(S,S)-3-[2-(6-Chloro-4-oxo-4H-quinazolin-3-yl)-butyrylamino]-4-oxo-5-(2,3,5,6-tetrafluoro-phenoxy) pentanoic acid

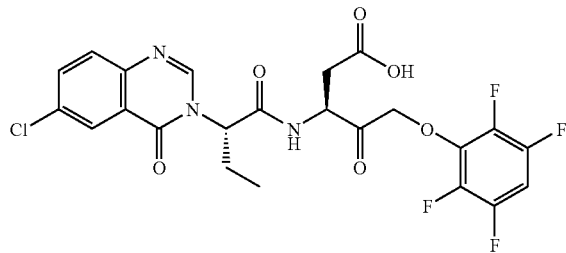

This compound was prepared using procedures similar to those described in methods F, G, and E. The title compound was obtained as a white solid (TFA salt) (94%, last step). IR (solid) 3298.7, 1741.4, 1691.4, 1660.3, 1601.1, 1517.4, 1490.8, 1320.6, 1244.7, 1174.5, 1104.4, 939.2, 836.5, 715.5, 666.8 and 656.0 cm$^{-1}$; $^1$H NMR (400 MHz, DMSO-d$_6$) δ 9.05 (1H, m), 8.4 (1H, s), 8.05-7.5 (4H, m), 5.45-5.15 (3H, m), 4.6 (1H, m), 2.25-2.0 (2H, m) and 0.9-0.75 (3H, m) ppm; $^{19}$F NMR (376 MHz, DMSO-d$_6$) (proton decoupled) δ −140.57, −140.59, −140.63, −140.65, −141.02, −141.04, −141.08, −141.10, −156.75, −156.77, −156.81, −156.83, −156.94, −156.96, −157.00, −157.02; MS ES (+) 544.2 (M+H).

EXAMPLE 6

(S,S)-4-Oxo-3-[2-(4-oxo-4H-quinazolin-3-yl)-butyrylamino]-5-(2,3,5,6-tetrafluoro-phenoxy)pentanoic acid

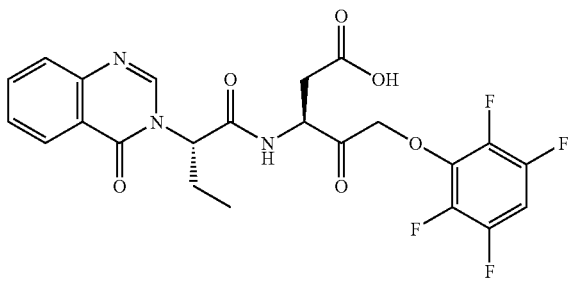

This compound was prepared using 2-(4-oxo-4H-quinazoline-3-yl)-butyric acid (synthesized from 2-nitrobenzoic acid using procedures similar to those described in methods K-M and E) and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The title compound was obtained as a white solid (TFA salt) (85%, last step). IR (solid) 1792.8, 1726.3, 1669.9, 1521.4, 1485.6, 1183.5, 1142.5, 1091.3 and 932.5 cm$^{-1}$; $^1$H NMR (400 MHz, DMSO-d$_6$) δ 9.0-8.65 (1H, m), 8.35 (1H, s), 8.1 (1H, m), 7.8 (1H, m), 7.65 (1H, m), 7.55 (2H, m), 5.4-4.3 (4H, m), 2.8-2.5 (2H, m), 2.2-2.0 (2H, m) and 0.9-0.7 (3H, m) ppm; $^{19}$F NMR (376 MHz, DMSO-d$_6$) (proton decoupled) δ −140.57, −140.60, −140.63, −140.66, −141.03, −141.05, −141.09, −141.11, −156.77, −156.80, −156.83, −156.86, −156.94, −156.97, −157.00, −157.03; MS ES (+) 510.26 (M+H).

EXAMPLE 7

(S,S)-4-Oxo-3-[2-(4-oxo-4H-quinazolin-3-yl)-butyrylamino]-5-(2,4,6-trifluoro-phenoxy)-pentanoic acid

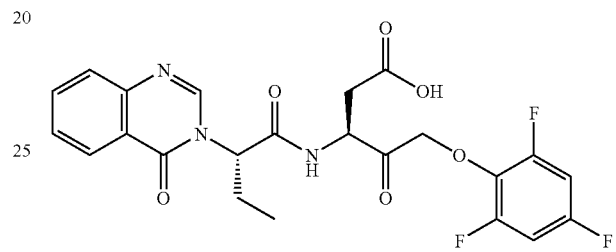

This compound was prepared using 2-(4-oxo-4H-quinazoline-3-yl)-butyric acid (synthesized from 2-nitrobenzoic acid using procedures similar to those described in methods K-M and E) and (3S)-3-amino-4-hydroxy-5-(2,4,6-trifluoro-phenoxy)-pentanoic acid tert-butyl ester (prepared from 2,4,6-trifluorophenol using procedures similar to those described in methods N-P) using procedures similar to those described in methods F, G and E. The title compound was obtained as a white solid (TFA salt) (71%, last step). IR (solid) 3308.9, 3075.4, 2928.4, 1803.1, 1726.9, 1672.7, 1612.1, 1510.0, 1478.7, 1452.8, 1407.6, 1231.3, 1199.3, 1121.0, 1040.4, 997.6, 933.1, 839.7, 772.9, 720.3 and 698.4 cm$^{-1}$; $^1$H NMR (400 MHz, DMSO-d$_6$) δ 0.84-0.86 (3H, m), 2.04-2.95 (4H,), 4.05-5.48 (5H, 6), 7.13-7.21 (2H, m), 7.54-7.57 (1H, m), 7.69-7.72 (1H, m), 7.84-7.88 (1H, m), 8.07-8.13 (1H, m), 8.38 (1H, s), 8.60-8.97 (1H, 2×dd) ppm; $^{19}$F NMR (376 MHz, DMSO-d$_6$) (proton decoupled) δ −115.4, −115.6, −124.9, −125.0, −125.6; MS ES (+): 492.3 (M+H).

EXAMPLE 8

(S,S)-4-Oxo-3-[2-(4-oxo-4H-quinazolin-3-yl)-butyrylamino]-5-(2,5,6-trifluoro-phenoxy)-pentanoic acid

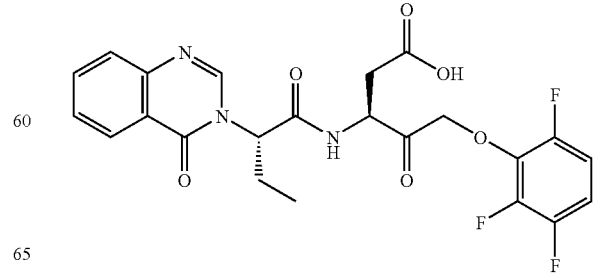

This compound was prepared using 2-(4-oxo-4H-quinazoline-3-yl)-butyric acid (synthesized from 2-nitrobenzoic acid using procedures similar to those described in methods K-M and E) and (3S)-3-amino-4-hydroxy-5-(2,3,6-trifluoro-phenoxy)-pentanoic acid tert-butyl ester (prepared from 2,3,6-trifluorophenol using procedures similar to those described in methods N-P) using procedures similar to those described in methods F, G and E. The title compound was obtained as a white solid (TFA salt)(87%, last step). IR (solid) 3308.9, 3075.4, 2928.4, 1803.1, 1726.9, 1672.7, 1612.1, 1510.0, 1478.7, 1452.8, 1407.6, 1231.3, 1199.3, 1121.0, 1040.4, 997.6, 933.1, 839.7, 772.9, 720.3 and 698.4 cm$^{-1}$; $^1$H NMR (400 MHz, DMSO-d$_6$) δ 0.84-0.86 (3H, m,), 2.04-2.95 (4H, 3 m), 4.05-5.48 (5H, 6×m), 7.13-7.21 (2H, m,), 7.54-7.57 (1H, m), 7.69-7.72 (1H, m), 7.84-7.88 (1H, m), 8.07-8.13 (1H, m), 8.38 (1H, s), 8.60-8.97 (1H, 2) ppm; $^{19}$F NMR (376 MHz, DMSO) (proton decoupled) δ −115.4, −115.6, −124.9, −125.0, −125.6; MS ES (+): 492.3 (M+H).

EXAMPLE 9

(S,S)-3-[2-(1-oxo-1H-isoquinolin-2-yl)-butyrylamino]-4-oxo-5-(2,3,5,6-tetrafluoro-phenoxy)-pentanoic acid

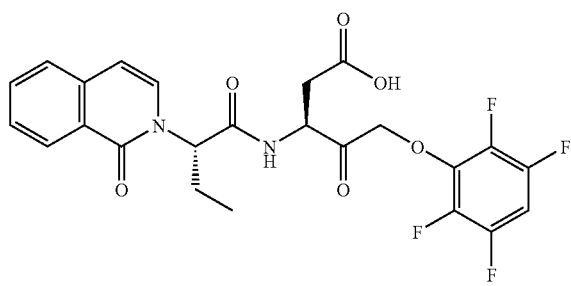

This compound was prepared using (S)-2-(1-oxo-1H-isoquinolin-2-yl)-butyric acid (prepared from 2-formylbenzoic acid using procedures similar to those described in methods A-E) and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The title compound was isolated by preparative HPLC. IR (solid) 2960.2, 1780.1, 1746.2, 1646.6, 1619.0, 1589.1, 1517.4, 1490.3, 1427.8, 1260.3, 1206.2, 1176.3, 1098.9, 938.4, 788.1, 748.3, 714.2, 692.5, 665.3 and 655.8 cm$^{-1}$; $^1$H NMR (400 MHz, DMSO-d$_6$) δ 0.78-0.83 (3H, m), 1.89-1.96 (1H, m), 2.08-2.13 (1H, m), 2.50-2.78 (2H, m), 4.35-5.45 (4H, 3×m), 6.64-6.69 (1H, m), 7.74-7.73 (5H, m), 8.18-8.20 (1H, m), 8.81 & 8.90 (1H, d) ppm; $^{19}$F NMR (376 MHz, DMSO) (proton decoupled) δ −141.01, −141.03, −141.07, −141.09, −156.80, −156.82, −156.86, −156.88; MS ES (+) 509.2 (M+H).

EXAMPLE 10

(S,S)-3-[2-(7-chloro-1-oxo-1H-isoquinolin-2-yl)-butyrylamino]-4-oxo-5-(2,3,5,6-tetrafluoro-phenoxy)-pentanoic acid

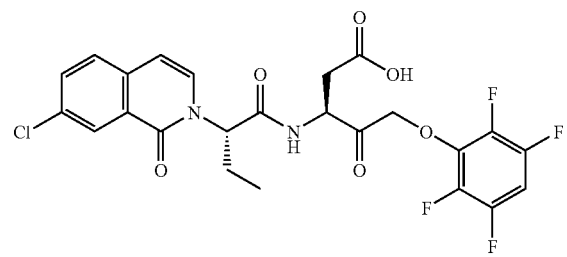

This compound was prepared using (S)-2-(7-chloro-1-oxo-1H-isoquinolin-2-yl)-butyric acid (prepared as described in methods A-E) and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The product was isolated as a white solid (94% last step). IR (solid) 1639.3, 1618.8, 1593.2, 1516.4, 1485.6, 1219.4, 1168.1, 1106.7, 932.6, 830.2 cm$^{-1}$; $^1$H NMR (400 MHz, DMSO-d$_6$) δ 0.80 (3H, t), 1.94-2.12 (2H, m), 2.55-2.61 (1H, m), 2.74-2.80 (1H, m), 4.58-4.63 (1H, m), 5.12-5.76 (3H, m), 6.70 (1H, d), 7.51-7.78 (4H, m), 8.11-8.12 (1H, m), 8.60-8.95 (1H, 2×d) ppm; $^{13}$C NMR (100 MHz, d$_6$-DMSO) δ 23.8, 24.5, 32.9, 34.6, 47.8, 52.8, 55.2, 58.2, 58.9, 74.4, 75.6, 100.1, 100.3, 100.5, 101.0, 101.2, 104.6, 126.5, 136.6, 131.3, 131.4, 133.0, 135.6, 135.6, 139.0, 139.1, 141.4, 141.6, 144.6, 144.8, 144.9, 147.1, 147.1, 160.7, 170.4, 172.0, 173.0, 202.2; $^{19}$F NMR (376 MHz, d$_6$-DMSO) (proton decoupled) δ −140.57, −140.60, −140.64, −140.66, −141.00, −141.03, −141.06, −141.09, −156.78, −156.80, −156.84, −156.86, −156.96, −156.98, −157.02, −157.04; MS ES (+) 543.20 (M+H).

EXAMPLE 11

(S,S)-3-[2-(6,7-dichloro-1-oxo-1H-isoquinolin-2-yl)-butyrylamino]-4-oxo-5-(2,3,5,6-tetrafluoro-phenoxy)-pentanoic acid

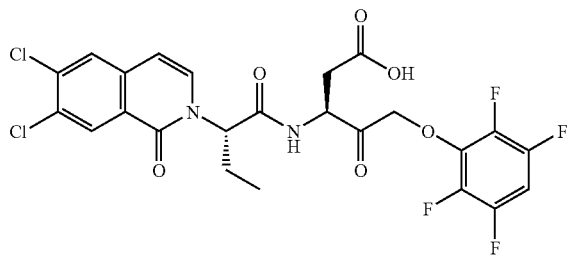

Method Q:

5,6-Dichloro-3H-isobenzofuran-1-one

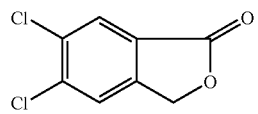

NaBH₄ (5.2 g) was added to a stirred solution of 4,5-dichlorophthalic anhydride (20 g) in anhydrous DMF (100 mL) at 0° C. under nitrogen in small portions over 1 hour. The reaction was warmed to room temperature for a further 2 hours and poured into ice/1M HCl. The resultant white precipitate (4,5-dichloro-2-hydroxymethyl-benzoic acid) was collected by filtration and dried under vacuum. The precipitate was suspended in toluene (200 mL) with catalytic p-toluenesulfonic acid and heated to reflux under Dean-Stark conditions (precipitate dissolves on heating) for 18 hours. The reaction was cooled to room temperature and the resultant white precipitate collected by filtration to give the sub-title compound as a white solid (14.0 g, 75%). $^1$H NMR (400 MHz, d$_6$-DMSO) δ 5.40 (2H, s), 8.05 (1H, s), 8.15 (1H, s) ppm.

Method R:

3-Bromo-5,6-dichloro-3H-isobenzofuran-1-one

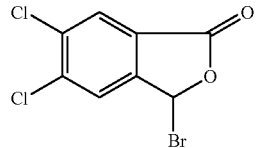

A suspension of 5,6-Dichloro-3H-isobenzofuran-1-one (1.45 g), N-bromosuccinamide (1.27 g) and catalytic benzoyl peroxide in chloroform (30 mL) was heated to reflux for 1 hour. After cooling, the reaction mixture was washed with water, brine, dried (magnesium sulfate), filtered and concentrated to give the sub-title compound as a white solid (1.82 g, 91%). $^1$H NMR (400 MHz, CDCl$_3$) δ 7.36 (1H, s), 7.77 (1H, s), 8.03 (1H, s) ppm.

Method S:

4,5-Dichloro-2-formyl-benzoic acid

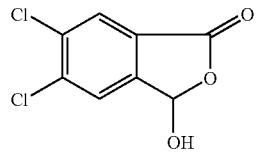

A suspension of 3-bromo-5,6-dichloro-3H-isobenzofuran-1-one (2.0 g) in 5% aqueous HCl (10 mL) and 80% aqueous dioxane (25 mL) was heated to reflux for 2 hours. The solvent was removed and the resulting residue re-dissolved in ethyl acetate, dried (magnesium sulfate) and concentrated. The resultant yellow solid was recrystallized from DCM/hexane to give the sub-title compound as a white solid (1.13 g, 73%). $^1$H NMR (400 MHz, CDCl$_3$) δ 6.66 (0.84H, s), 7.95 (0.16H, s), 8.05 (0.84H), 8.12 (0.16H, s), 8.14 (0.84H, s), 8.41 (0.84H,), 10.41 (0.16H, s), 11.07 (0.16H, brd s) ppm.

(S,S)-3-[2-(6,7-dichloro-1-oxo-1H-isoquinolin-2-yl)-butyrylamino]-4-oxo-5-(2,3,5,6-tetrafluoro-phenoxy)-pentanoic acid

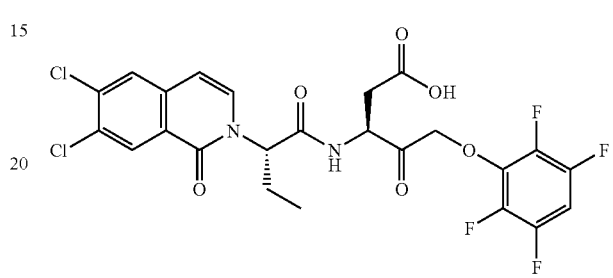

This compound was prepared using (S)-2-(6,7-dichloro-1-oxo-1H-isoquinolin-2-yl)-butyric acid (synthesized from 4,5-dichloro-2-formyl-benzoic acid [prepared as described in methods Q-S] using procedures similar to those described in methods A-E) and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The title compound was isolated as a white solid (94% last step). IR (solid) 1784.5, 1734.7, 1650.1, 1610.2, 1585.4, 1515.7, 1490.8, 1426.0, 1216.9, 1172.1, 1092.5, 933.1 cm$^{-1}$; $^1$H NMR (400 MHz, d$_6$-DMSO) δ 0.80 (3H, t), 1.90-1.98 (1H, m), 2.04-2.12 (1H, m), 2.55-2.79 (2H, m), 4.56-4.71 (1H, m), 5.08-5.41 (3H, m), 6.67 (1H, d), 7.56-7.59 (2H, m), 8.07 (1H, brd s), 8.25 (1H, d) 8.85-8.95 (1H, 2×d), 12.73 (1H, brd s) ppm; $^{19}$F NMR (376 MHz, d$_6$-DMSO) (proton decoupled) δ −140.93, −140.95, −140.99, −141.01, −141.04, −141.07, −141.10, −156.76, −156.79, −156.82, −156.85, −156.89, −156.91; MS ES (+) 577.14 (M+H).

EXAMPLE 12

3-[(2S)-2-[6-(2-Chloro-phenoxy)-4-oxo-4H-quinazolin-3-yl)-butyrylamino]-5-fluoro-4-oxo-pentanoic acid

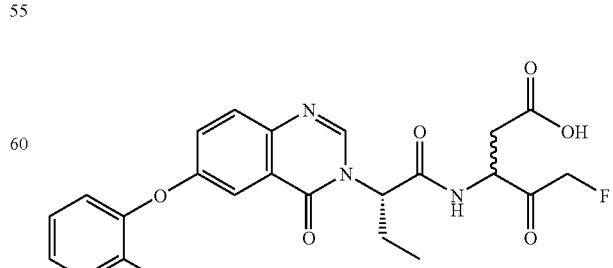

Method T:

2-Nitro-5-(2-chlorophenoxy)methyl benzoate

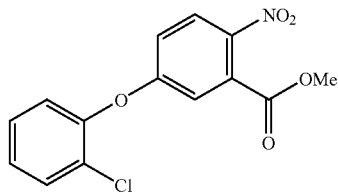

To a stirred solution of 5-chloro-2-nitrobenzoic acid methyl ester (1 g, 4.6 mmol) in dimethylformamide (15 ml), was added potassium carbonate (0.96 g), and 2-chlorophenol (0.66 g). The reaction mixture was stirred at 90° C. for 16 hours. After this time the reaction mixture was poured into ethyl acetate (50 ml) and washed with water (50 ml), brine (50 ml), dried (MgSO$_4$), and evaporated. The residue was purified by flash chromatography (1:9 ethyl acetate: pet ether) to give the sub-titled compound as a yellow oil (1.22 g, 85% yield). $^1$H NMR (400 MHz, CDCl$_3$) δ 8.05 (1H, m), 7.6-7.0 (6H, m), 3.95 (3H, s) ppm.

Method U:

2-Nitro-5-(2-chlorophenoxy)benzoic acid

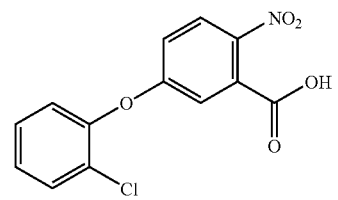

To a stirred solution of 2-nitro-5-(2-chlorophenoxy)methyl benzoate (1.22 g) in THF (8 ml) was added lithium hydroxide (0.333 g) in water (2 ml). The reaction mixture was stirred at ambient temperature for 16 hours. After this time the reaction mixture was acidified with aqueous 1M HCl. The aqueous layer was extracted with ethyl acetate (2×50 ml). The organics were combined and washed with saturated brine solution and dried (MgSO$_4$). The solvents were removed under vacuum to give the sub-title compound as an off-white solid (0.63 g, 54% yield). $^1$H NMR (400 MHz, MeOD) δ 8.05-7.0 (7H, m) ppm.

3-[(2S)-2-[6-(2-Chloro-phenoxy)-4-oxo-4H-quinazolin-3-yl)-butyrylamino]-5-fluoro-4-oxo-pentanoic acid

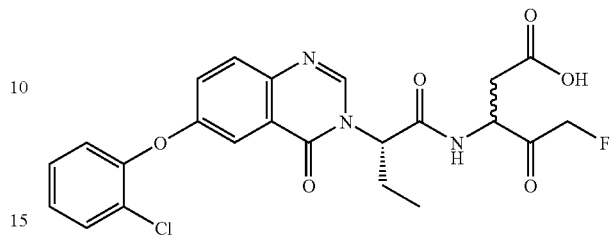

This compound was prepared from 2-(6-[2-chlorophenoxy]-4-oxo-4H-quinazoline-3-yl)-butyric acid, (synthesized from 5-chloro-2-nitrobenzoic acid methyl ester and 2-chlorophenol as described in methods T-U, K-M and E) using procedures similar to those described in methods F, G and E. The title compound was obtained as a white solid (TFA salt) (82%, last step). IR (solid) 1783.38, 1721.55, 1664.48, 1550.32, 1498.00, 1474.22, 1264.94, 1193.60, 1136.52, 1055.66 cm$^{-1}$; $^1$H NMR (400 MHz, DMSO-d$_6$) δ 0.81 (3H, m), 1.95-2.26 (2H, m), 2.50-2.96 (2H, m), 4.20-4.70 (1.5H, m), 5.04-5.46 (2.5H, m), 7.26-7.39 (3H, m), 7.45 (1H, m), 7.57-7.70 (2H, m), 7.78 (1H, m), 8.35 (1H, m), 8.63-8.98 (1H, brm) ppm; $^{19}$F NMR (376 MHz, DMSO-d$_6$) (proton decoupled) δ −226.73, −226.78, −230.43, −230.90, −232.64, −232.55; MS ES (+) 490.40 (M+H).

EXAMPLE 13

3-[(2S)-2-[6-(3-Chlorophenoxy)-4-oxo-4H-quinazolin-3-yl)-butyrylamino]-5-fluoro-4-oxo-pentanoic acid

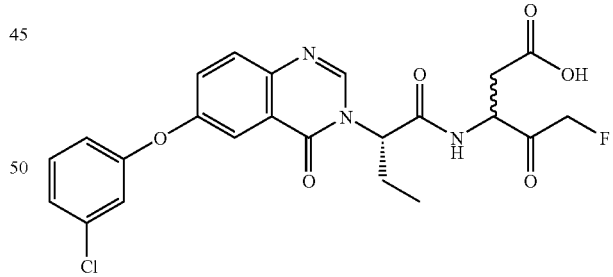

This compound was prepared from 2-(6-[3-chlorophenoxy]-4-oxo-4H-quinazoline-3-yl)-butyric acid, (synthesized from 5-chloro-2-nitrobenzoic acid methyl ester and 3-chlorophenol using methods similar to those described in T-U, K-M and E) using procedures similar to those described in methods F, G and E. The product was obtained as a white solid (TFA salt) (85%, last step). IR (solid) 1716.79, 1673.99, 1583.62, 1469.46, 1279.21, 1198.35, 1136.52 cm$^{-1}$; $^1$H NMR (400 MHz, DMSO-d$_6$) δ 0.75-0.9 (3H, m), 1.95-2.2 (2H, m), 2.5-2.9 (2H, m), 4.2-4.7 (2H, m), 5.05-5.45 (2H, m), 7.1 (1H, m), 7.25 (1H, m), 7.3 (1H, m), 7.45 (1H, m), 7.55

(1H, m), 7.6 (1H, m), 7.8 (1H, m), 8.35 (1H, m), and 8.65-9.0 (1H, m) ppm; $^{13}$C NMR (100 MHz, DMSO-d$_6$) δ 202.6, 202.5, 173.1, 172.0, 172.0, 170.0, 169.8, 169.8, 160.2, 160.1, 158.8, 157.4, 155.3, 144.1, 134.5, 132.1, 130.1, 126.6, 124.6, 122.6, 122.5, 119.7, 118.2, 113.7, 85.3, 85.2, 83.5, 83.4, 82.9, 58.2, 57.8, 57.5, 53.0, 52.3, 52.2, 47.8, 34.6, 33.0, 24.4, 23.8 and 10.66; $^{19}$F NMR (376 MHz, DMSO-d$_6$) (proton decoupled) δ −226.72, −226.78, −230.90 and −232.65; MS ES (+) 490.25 (M+H).

EXAMPLE 14

5-Fluoro-3-{(2S)-2[6-(3-fluorophenoxy)-4-oxo-4H-quinazolin-3-yl]-butyrylamino}-4-oxo-pentanoic acid

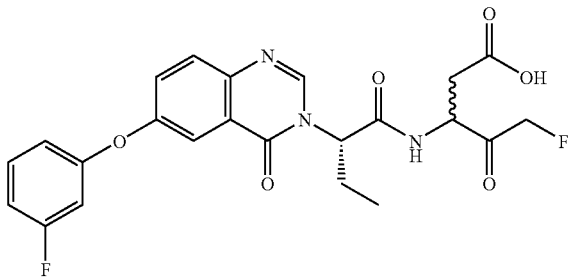

This compound was prepared from 2-[6-(3-fluorophenoxy)-4-oxo-4H-quinazolin-3-yl]-butyric acid, (synthesized from 5-chloro-2-nitrobenzoic acid methyl ester and 3-fluorophenol using methods similar to those described in T-U, K-M and E) using procedures similar to those described in methods F, G and E. The product was obtained as a white solid (TFA salt) (95%, last step). IR (solid) 1598.20, 1274.17, 1178.86, 1159.80, 1116.92 and 954.90 cm$^{-1}$; $^1$H NMR (400 MHz, DMSO-d$_6$) δ 0.8-0.95 (3H, m), 1.95-2.2 (2H, m), 2.55-2.95 (2H, m), 4.2-4.7 (2H, m), 5.05-5.5 (2H, m), 6.95 (1H, m), 7.05 (1H, m), 7.45 (1H, m), 7.55 (1H, m), 7.6 (1H, m), 7.8 (1H, m), 8.4 (1H, m), and 8.65-9.0 (1H, m) ppm; $^{13}$C NMR (100 MHz, DMSO-d$_6$) δ 172.0, 169.9, 169.8, 164.5, 162.1, 160.2, 155.3, 144.1, 132.0, 131.9, 130.0, 126.9, 122.6, 115.5, 113.7, 111.5, 111.3, 107.4, 107.1, 85.3, 58.2, 57.8, 52.4, 52.2, 34.6, 23.8, and 10.7; $^{19}$F NMR (376 MHz, DMSO-d$_6$) (proton decoupled) δ −110.84, −226.73, −226.79, −230.41, −230.91, −232.64 and −232.66; MS ES (+) 474.29 (M+H).

EXAMPLE 15

3-{(2S)-2-[6-(2,4-Dichloro-phenoxy)-4-oxo-4H-quinazolin-3-yl]-butyrylamino}-5-fluoro-4-oxo-pentanoic acid

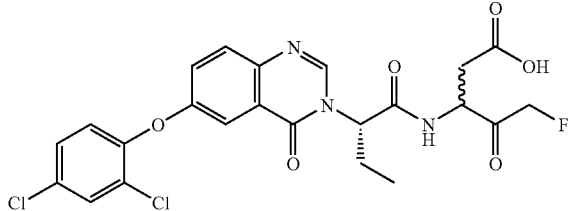

This compound was prepared from 2-[6-(2,4-dichlorophenoxy)-4-oxo-4H-quinazolin-3-yl]-butyric acid, (synthesized from 2-nitro-5-2,4-dichlorophenoxybenzoic acid methyl ester using methods similar to those described in U, K-M and E) using procedures similar to those described in methods F, G and E. The product was obtained as a white solid (TFA salt)(96%, last step). IR (solid) 1778.63, 1716.79, 1669.23, 1493.25, 1469.46, 1264.94, 1198.35, 1150.79, 1098.47 and 1055.66 cm$^{-1}$; $^1$H NMR (400 MHz, DMSO-d$_6$) δ 0.60-1.05 (3H, m), 1.94-2.26 (2H, m), 2.26-2.95 (2H, m), 4.15-4.75 (2H, m), 4.76-5.95 (2H, m), 7.25-7.45 (2H, m), 7.50 (1H, m), 7.65 (1H, m), 7,80 (1H, m), 7.87 (1H, m), 8.36 (1H, s), 8.60-9.01 (1H, brm) ppm; $^{19}$F NMR (376 MHz, DMSO-d$_6$) (proton decoupled) δ −226.72, −226.77, −230.41, −230.88, −232.65; MS ES (+) 524.34 (M+H).

EXAMPLE 16

5-Fluoro-4-oxo-3-[(2S)-2-(4-oxo-6-phenylsulfanyl-4H-quinazolin-3-yl)-butyrylamino]-entanoic acid

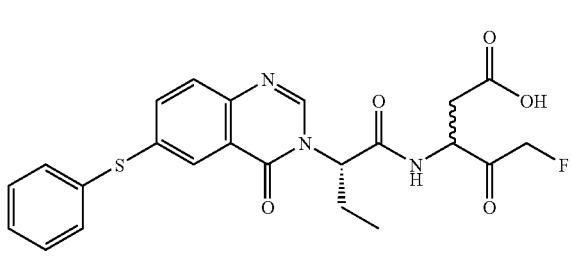

This compound was prepared from (S)-2(4-oxo-6-phenylsulfanyl-4H-quinazolin-3-yl)-butyric acid, (synthesized from 5-chloro-2-nitrobenzoic acid methyl ester and thiophenol using methods similar to those described in T-U, K-M and E) using procedures similar to those described in methods F, G and E. The product was obtained as a white solid (TFA salt)(81%, last step). IR (solid) 1791.61, 1720.53, 1668.40, 1602.06, 1545.20, 1474.12, 1194.53, 1142.41 and 1057.11 cm$^{-1}$; $^1$H NMR (400 MHz, DMSO-d$_6$) δ 9.6-8.6 (1H, m), 8.3 (1H, s), 7.85 (1H, s), 7.75-7.6 (2H, m), 7.45-7.35 (5H, m), 5.4-5.0 (2H, m), 4.6-4.15 (2H, m), 2.85-2.35 (2H, m), 2.2-1.95 (2H, m) and 0.85-0.7 (3H, m) ppm; $^{13}$C NMR (100 MHz, DMSO-d$_6$) δ 202.6, 202.5, 173.1, 172.0, 172.0, 169.9, 169.8, 160.0, 146.5, 136.1, 135.4, 133.6, 133.3, 130.3, 128.8, 128.7, 126.7, 126.6, 122.2, 122.2, 104.0, 85.3, 85.2, 83.5, 83.4, 58.3, 57.9, 57.4, 52.3, 52.2, 47.8, 34.6, 33.0, 24.4, 23.9, 23.8 and 10.6; $^{19}$F NMR (376 MHz, DMSO-d$_6$) (proton decoupled) δ −226.72, −226.78, −230.41, −231.92, −232.65 and −232.68; MS ES (+) 472.27 (M+H).

EXAMPLE 17

5-Fluoro-3{(2S)-2[6-(3-fluoro-phenylsulfanyl)-4-oxo-4H-quinazolin-3-yl]-butyrylamino}-4-oxo-pentanoic acid

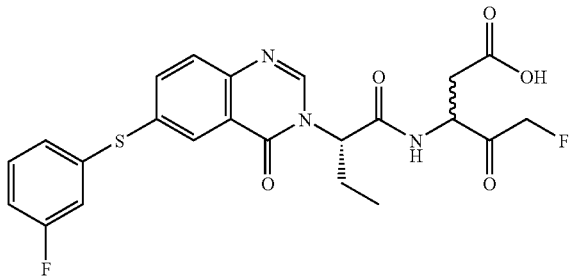

This compound was prepared from (S)-2[6-(3-fluoro-phenylsulfanyl)-4-oxo-4H-quinazolin-3-yl]-butyric acid (synthesized from 5-chloro-2-nitrobenzoic acid methyl ester and 3-fluorothiophenol using methods similar to those described in T-U, K-M and E) using procedures similar to those described in methods F, G and E. The product was obtained as a white solid (TFA salt)(95%, last step). IR (solid) 1779.2, 1722.0, 1660.1, 1602.9, 1574.3, 1474.3, 1178.8 and 1059.7 cm$^{-1}$; $^1$H NMR (400 MHz, DMSO-$d_6$) δ 0.80 (3H, m), 1.92-2.25 (2H, m), 2.41-2.92 (2H, m), 4.20-4.85 (1.5H, m), 5.01-5.50 (2.5H, m), 7.12-7.27 (3H, m), 7.40-7.50 (1H, m), 7.70-7.86 (2H, m), 8.03 (1H, m), 8.43 (1H, m), 8.65-9.02 (1H, brm) ppm; $^{19}$F NMR (376 MHz, DMSO-$d_6$) (proton decoupled) δ −111.83, −226.73, −226.79, −230.40, −230.91, −232.65, −232.67; MS ES (+) 490.35 (M+H).

EXAMPLE 18

(S)-3-[2-(7-chloro-1-oxo-1H-isoquinolin-2-yl)-3-methylbutyrylamino]-5-fluoro-4-oxo-pentanoic acid

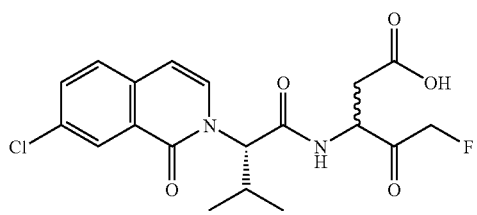

This was prepared using procedures similar to those described in methods A-G (S-valine tert-butyl ester was used in method C). The product was isolated as a white solid (91% last step). IR (solid) 1777.5, 1644.4, 1608.5, 1588.1, 1541.9, 1198.9, 1168.1, 1045.2, 830.2 cm$^{-1}$; $^1$H NMR (400 MHz, $d_6$-DMSO) δ 0.70 (3H, m), 0.89-1.14 (3H, m), 2.31 (1H, m), 2.45-2.98 (2H, m), 4.05-4.75 (1.6H, m), (2.4H, m), 6.70 (1H, m), 7.60-7.95 (3H, m), 8.18 (1H, m), 8.75-9.21 (1H, m) ppm; $^{19}$F NMR (376 MHz, $d_6$-DMSO) (proton decoupled) δ −226.28, −226.71, −230.58, −230.64, −231.75, −232.32; MS ES (+) 411.36 (M+H).

EXAMPLE 19

(S,S)-3-[2-(7-trifluoromethyl-1-oxo-1H-isoquinolin-2-yl)-butyrylamino]-4-oxo-5-(2,3,5,6-tetrafluoro-phenoxy)-pentanoic acid

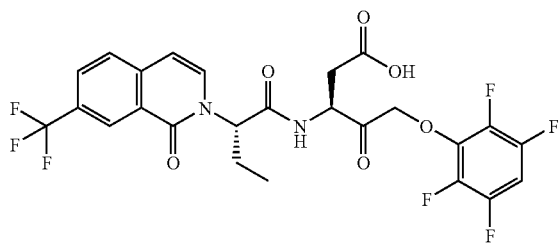

This compound was prepared using (S)-2-(7-trifluoromethyl-1-oxo-1H-isoquinolin-2-yl)-butyric acid (prepared as described in methods A-E, see example 2) and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The product was isolated as a white solid (90% last step). IR (solid) 1791.6, 1649.5, 1516.8, 1493.1, 1322.5 cm$^{-1}$; $^1$H NMR (400 MHz, $d_6$-DMSO) δ 0.85 (3H, t), 1.90-2.20 (2H, 2×m), 2.50-2.90 (2H, 2×m), 4.70 (1H, m), 5.25 (2H, dd), 5.45 (1H, m), 6.80 (1H, d), 7.65 (1H, m), 7.70 (1H, d), 7.95 (1H, d), 8.05 (1H, d), 8.45 (1H, s), 9.00 (1H, d) ppm; $^{19}$F NMR (376 MHz, $d_6$-DMSO) (proton decoupled) δ −56.60, −70.15, −136.38, −152.08.

EXAMPLE 20

(S,S)-3-[2-(7-trifluoromethyl-4-oxo-4H-quinazolin-3-yl)-butyrylamino]-4-oxo-5-(2,3,5,6-tetrafluoro-phenoxy)pentanoic acid

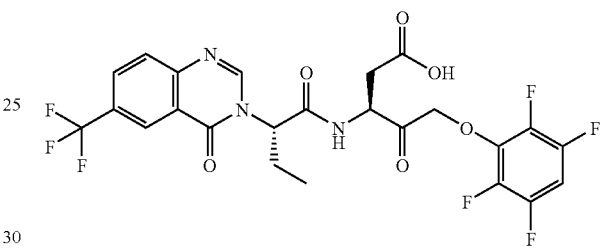

Method V:

(S)-2-(2-Benzylamino-5-trifluoromethyl-benzoylamino)-butyric acid tert-butyl ester

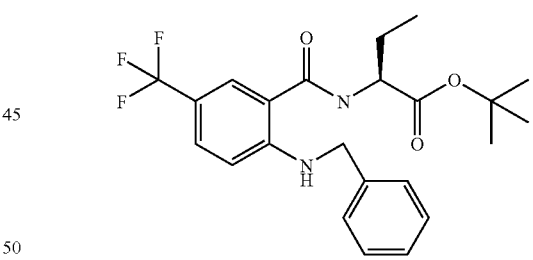

To a solution of (S)-2-(2-chloro-5-trifluoromethyl-benzoylamino)-butyric acid tert-butyl ester (prepared from 2-chloro5-trifluoromethylbenzoic acid and (S)-2-aminobutyric acid, tert butyl ester in a procedure similar to that described in method F) (3 g) and benzylamine (1.1 ml) in N-methylpyrrolidine (40 ml) was added potassium carbonate (1.6 g), copper (30 mg) and copper (I) bromide (15 mg). The mixture was heated at 160° C. for 3 hours then cooled to room temp. and diluted with saturated ammonium chloride solution. The mixture was extracted with ethyl acetate and the organic solution dried (magnesium sulfate), filtered and concentrated. The residue was purified on silica gel, eluting with 15% ethyl acetate/hexane. The sub-titled product was obtained as a white solid (950 mg, 27%). $^1$H NMR (400 MHz, CDCl$_3$) δ 1.04 (3H, t), 1.50 (9H, s), 2.86 (1H, m), 2.02 (1H, m), 4.50 (2H, d), 4.65 (1H, m), 6.69 (2H, m), 7.21-7.70 (7H, m), 8.42 (1H, m) ppm; MS ES (−) 435.32 (M−H).

(S)-2-(6-trifluoromethyl-4-oxo-4H-quinazoline-3-yl)-butyric acid

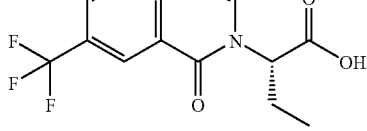

This compound was prepared from (S)-2-(2-benzylamino-5-trifluoromethyl-benzoylamino)-butyric acid tert-butyl ester using procedures similar to those described in methods P, M and E. The sub-title compound was as a white solid. $^1$H NMR (400 MHz, $d_6$-DMSO) δ 0.88 (3H, t), 2.22 (2H, m), 5.15 (1H, m), 7.95 (1H, m), 8.20 (1H, m), 8.40 (1H, s), 8.60 (1H, s) ppm; MS ES (+) 301.15 (M+H).

(S,S)-3-[2-(7-trifluoromethyl-4-oxo-4H-quinazolin-3-yl)-butyrylamino]-4-oxo-5-(2,3,5,6-tetrafluoro-phenoxy)pentanoic acid

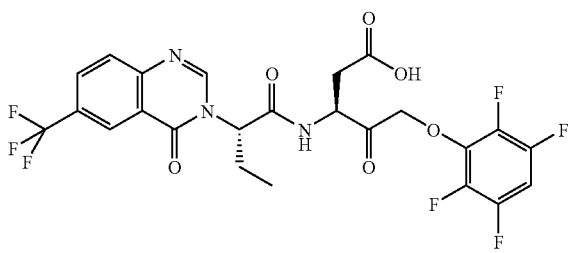

This compound was prepared from 2-(6-trifluoromethyl-4-oxo-4H-quinazoline-3-yl)-butyric acid and (3S)-3-amino-4-hydroxy-5-(2,3,5,6-tetrafluoro-phenoxy)-pentanoic acid tert-butyl ester (prepared as described in methods N-P) using procedures similar to those described in methods F, G and E. The titled compound was obtained as a white solid (TFA salt) (90% last step). IR (solid) 1690, 1518, 1490, 1317, 1254, 1170, 1128 cm$^{-1}$; $^1$H NMR (400 MHz, $d_6$-DMSO) δ 0.8-0.9 (3H, m), 2.05-2.2 (2H, m), 2.57-2.80 (2H, m), 4.55-4.62 (2H, m), 5.20-5.35 (3H, m), 7.50-7.62 (1H, m), 7.95 (1H, d), 8.20 (1H, d), 8.38 (1H, m), 8.52 (1H, s), 9.04 (1H, d) ppm; MS ES (+) 578.2 (M+H).

EXAMPLE 21

(S)-3-[2-(7-phenyl-1-oxo-1H-isoquinolin-2-yl)-butyrylamino]-5-fluoro-4-oxo-pentanoic acid

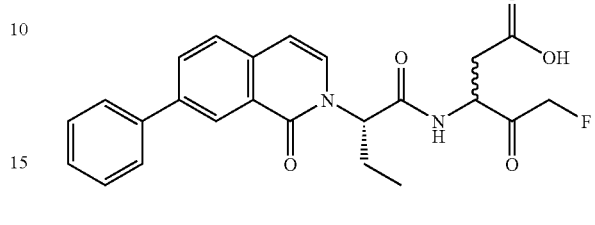

Method W:

(S)-2-(7-phenyl-1-oxo-1H-isoquinolin-2-yl)-butyric acid

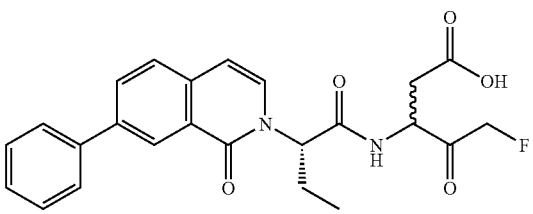

To a solution of (S)-2-(7-chloro-1-oxo-1H-isoquinolin-2-yl)-butyric acid (prepared as described in methods A-E) (200 mg) and phenyl boronic acid (276 mg) in THF (2 ml) was added palladium (II) acetate (1.7 mg), 2-(di-tert-butylphosphino)biphenyl (4.5 mg) and potassium fluoride (262 mg). The resulting mixture was heated at reflux for 18 hours, then cooled and diluted with 1M HCl (5 ml) and ethyl acetate (15 ml). The organic phase was separated and the aqueous extracted with ethyl acetate (2×15 ml). The combined organics were dried (magnesium sulfate), filtered and concentrated. The residue was purified through a plug of silica gel, then further purified by radial chromatography eluting with 1% acetic acid in ethyl acetate. This gave the subtitled product as a brown solid (153 mg, 66%). $^1$H NMR (400 MHz, CDCl$_3$) δ 1.00 (3H, t), 2.15 (1H, m), 2.40 (1H, m), 5.37 (1H, m), 6.70 (1H, d), 7.15 (1H, d), 7.45 (1H, m), 7.55 (2H, m), 7.68 (1H, m), 7.75 (2H, m), 7.99 (1H, d), 8.70 (1H, s) ppm.

(S)-3-[2-(7-phenyl-1-oxo-1H-isoquinolin-2-yl)-butyrylamino]-5-fluoro-4-oxo-pentanoic acid This compound was prepared from (S)-2-(7-phenyl-1-oxo-1H-isoquinolin-2-yl)-butyric acid using procedures similar to those described in methods F, G and E. The titled compound was obtained as a white solid (58% last step). $^1$H NMR (400 MHz, d$_6$-DMSO) δ 8.95-8.5 (1H, m), 8.45 (1H, s), 8.05 (1H, m), 7.8-7.7 (2H, m), 7.65-7.35 (4H, m), 6.7-6.65 (1H, m), 5.6-5.0 (2.4H, m), 4.7-4.2 91.6H, m), 2.9-2.3 (H, m), 2.15-1.85 (2H, m), 0.8-0.7 (3H, m) ppm; $^{13}$C NMR (100 MHz, DMSO-d$_6$) δ 202.8, 202.6, 173.2. 172.0, 170.6, 170.5, 161.7, 139.7, 138.7, 138.7, 136.1, 136.1, 131.0, 130.9, 130.8, 127.3, 125.8, 125.8, 125.7, 125.1, 105.1, 105.0, 104.8, 85.3, 85.2, 83.5, 83.4, 58.9, 58.5, 58.0, 52.3, 52.2, 47.6, 34.7, 34.6, 33.0, 32.9, 24.6, 24.1, 23.9; $^{19}$F NMR (376 MHz, d$_6$-DMSO) (proton decoupled) δ −226.68, −226.72, −230.50, −231.17, −232.60, −232.66; MS ES (+) 439.0 (M+H).

EXAMPLE 22

5-Fluoro-4-oxo-3-[(2S)-2-(4-oxo-6-propylsulfanyl-4H-quinazolin-3-yl)-butyrylamino]-pentanoic acid

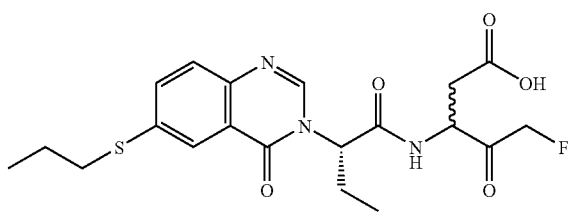

(S)-2-(4-oxo-6-propylsulfanyl-4H-quinazoline-3-yl)-butyric acid, tert-butyl ester

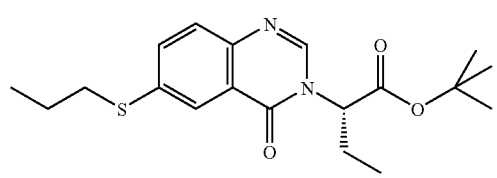

This compound was prepared from 5-chloro-2-nitrobenzoic acid methyl ester and propanethiol using procedures similar to those described in methods T-U and K-M. The sub-title compound was as a solid. $^1$H NMR (400 MHz, CDCl$_3$) δ 1.00 (3H, t), 1.10 (3H, t), 1.51 (9H, s), 1.75 (2H, m), 2.01 (1H, m), 2,31 (1H, m), 3.03 (2H, m), 5.30 (1H, m), 7.60-7.70 (2H, m), 8.05 (1H, s), 8.13 (1H, s) ppm; MS ES (+) 363.29 (M+H).

5-Fluoro-4-oxo-3-[(2S)-2-(4-oxo-6-propylsulfanyl-4H-quinazolin-3-yl)-butyrylamino]-pentanoic acid

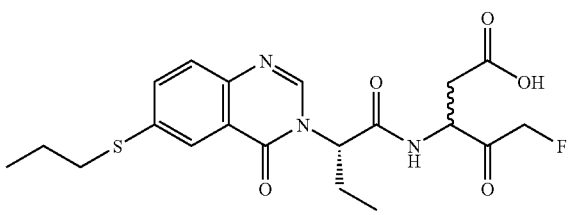

This compound was prepared from (S)-2-(4-oxo-6-propyl-sulfanyl-4H-quinazoline-3-yl)-butyric acid (synthesized from the tert-butyl ester using TFA/DCM) using a procedure similar to that described in method F. The resulting alcohol was oxidized using tetra-n-propylammonium perruthenate (VII)/N-methylmorpholine-N-oxide (*Synthesis*, 639 (1994)) and the tert-butyl ester deprotected as described in method E. The title compound was obtained as a white solid (90% last step) (TFA salt). IR (solid) 2963.9, 1786.2, 1739.4, 1666.8, 1195.2 cm$^{-1}$; $^1$H NMR (400 MHz, CDCl$_3$) δ 1.02 (3H, t), 1.08 (3H, t), 1.70-1.80 (2H, m), 2.02-2.09 (1H, m), 2.29-2.36 (1H, m), 2.72-2.92 (1H, m), 3.00-3.15 (1H, m), 3.03 (2H, t), 4.50-5.20 (3H, m), 5.40-5.60 (1H, m), 7.69-7.75 (2H, m), 8.06-8.07 (1H, m), 8.60-8.64 (1H, m) ppm; $^{19}$F NMR (376 MHz, CDCl$_3$) (proton decoupled) −76.23, −231.5; MS ES (+) 436.3 (M+H)

EXAMPLE 23

Enzyme Assays

The assays for caspase inhibition are based on the cleavage of a fluorogenic substrate by recombinant, purified human Caspases −1, −3, −7 or −8. The assays are run in essentially the same way as those reported by Garcia-Calvo et al., *J. Biol. Chem.* 273, 32608-32613 (1998), using a substrate specific for each enzyme. The substrate for Caspase-1 is Acetyl-Tyr-Val-Ala-Asp-amino-4-methylcoumarin and the substrate for Caspases −3, −7 and −8 is Acetyl-Asp-Glu-Val-Asp-amino-4-methylcoumarin both as disclosed in Garcia-Calvo et al., *J. Biol. Chem.* 273, 32608-32613 (1998).

The observed rate of enzyme inactivation at a particular inhibitor concentration, $k_{obs}$, is computed by direct fits of the data to the equation derived by Thornberry et al., *Biochemistry*, 33, 3943-3939 (1994) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression.

Table 2 shows inhibition of caspases −1, −3, and −8 activity for selected compounds of this invention as determined by the above method. Compounds with $k_{inact}(M^{-1}s^{-1})>500000$ are listed as "A". Compounds with $k_{inact}(M^{-1}s^{-1})$ between 100000 and 500000 are listed as "B". Compounds with $k_{inact}(M^{-1}s^{-1})<100000$ are listed as "C".

TABLE 2

Inhibition of Caspases-1, -3, and -8

| Compound Number | $k_{inact}$ Caspase-1 | Caspase-3 | Caspase-8 |
|---|---|---|---|
| 1 | A | A | B |
| 2 | A | A | A |
| 3 | B | B | C |
| 4 | B | B | C |
| 5 | A | A | B |
| 6 | B | A | C |
| 7 | C | B | C |
| 8 | B | B | C |
| 9 | B | B | C |
| 10 | A | A | C |
| 11 | A | A | C |
| 12 | A | A | A |
| 13 | B | B | A |
| 14 | A | A | B |
| 15 | B | B | A |
| 16 | A | A | A |
| 17 | A | A | A |
| 18 | B | B | C |
| 19 | A | A | C |
| 20 | A | A | C |
| 21 | A | A | A |
| 22 | A | A | A |

EXAMPLE 24

Inhibition of IL-1β Secretion from Whole Blood

Human blood is freshly drawn from healthy donors and diluted 1:2 in PBS. To 500 µl of diluted blood 50 ml of prediluted test compound in RPMI medium and 10 ml LPS (5 ng/ml final concentration on the plate) are added (LPS, Serotype 0111:B4, Sigma L3012). After stimulation for 18 hours supernatants are collected and assayed for IL-1β levels using the appropriate ELISA kit (R&D systems).

Table 3 below shows inhibition of IL-1β secretion from human whole blood for selected compounds of this invention as determined by the above methods. Compounds with an $IC_{50}$>10 µM are listed as "A". Compounds with an $IC_{50}$ between 1 µM and 10 uM are listed as "B". Compounds with an $IC_{50}$<1 µM are listed as "C".

TABLE 3

Inhibition of IL-1β secretion

| Compound Number | $IC_{50}$ (µm) |
|---|---|
| 1 | C |
| 2 | C |
| 3 | B |
| 4 | B |
| 5 | B |
| 6 | B |
| 7 | A |
| 8 | B |
| 9 | A |
| 10 | B |
| 11 | A |
| 12 | B |
| 13 | B |
| 14 | C |
| 15 | B |
| 16 | B |
| 17 | B |
| 18 | B |
| 19 | B |
| 20 | A |

TABLE 3-continued

Inhibition of IL-1β secretion

| Compound Number | $IC_{50}$ (µm) |
|---|---|
| 21 | B |
| 22 | C |

EXAMPLE 25

Hypoxia-Induced Apoptosis of Rat Cortical Neurons

Cortical neurons are dissociated from Wistar rat embryos (E17) by a modification of the procedure of Rogers et al., *Brain Res. Bulletin,* 44:131 (1998). Briefly, cerebral cortices are isolated aseptically from 15-20 Wistar rat embryos. A cell suspension is prepared by mincing the cerebral cortices and digesting them with papain. Cells are washed with ovomucoid enzyme inhibitor and DNaseI and plated onto Poly-D lysine coated plates in high glucose DMEM containing 10% heat-inactivated fetal calf serum, L-glutamine, penicillin and streptomycin. The yield of neurons is 10×7 per embryo and they are 80-90% viable as assessed by Trypan blue exclusion.

The neurons are cultured in complete medium at 37° C. in a normal atmosphere for 48 hours prior to the hypoxia experiments. For hypoxia, the normal cell medium is replaced by oxygen-depleted serum-free medium. Cells are incubated in an atmosphere of 95% $N_2$/5% $CO_2$ for various lengths of time. Compounds are dissolved in DMSO at 100 mM then diluted in medium and added to the culture from time=0. The level of apoptosis is measured using a Cell Death Detection ELISA kit (Roche) which detects DNA fragmentation. Plates are read at 405 nm. Controls included cells cultured in aerobic conditions in serum-containing medium (+serum) and cells cultured in aerobic conditions in serum-deprived medium (−serum).

Table 4 shows the results of the activity of selected compounds of this invention in the Hypoxia-induced apoptosis of rat cortical neurons. Compounds with an $IC_{50}$>0.5 µM are listed as "A". Compounds with an $IC_{50}$ between 0.1 µM and 0.5 uM are listed as "B". Compounds with an $IC_{50}$<0.1 µM are listed as "C".

TABLE 4

Activity in Hypoxia-induced Apoptosis Assay

| Compound Number | $IC_{50}$ (µm) |
|---|---|
| 1 | B |
| 2 | A |
| 3 | B |
| 4 | A |
| 5 | B |
| 6 | B |
| 7 | A |
| 8 | B |
| 9 | B |
| 10 | C |
| 11 | B |
| 12 | A |
| 13 | B |
| 14 | A |
| 15 | B |
| 16 | B |
| 17 | B |
| 18 | B |
| 19 | C |
| 20 | B |

TABLE 4-continued

Activity in Hypoxia-induced Apoptosis Assay

| Compound Number | IC$_{50}$ (μm) |
| --- | --- |
| 21 | B |
| 22 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example above.

We claim:

1. A compound selected from the group consisting of:

5.

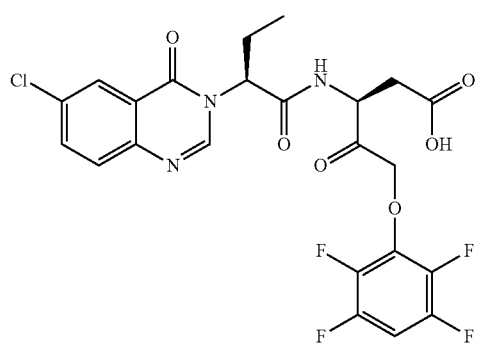

6.

7.

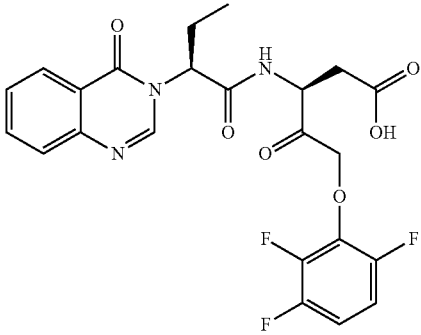

8.

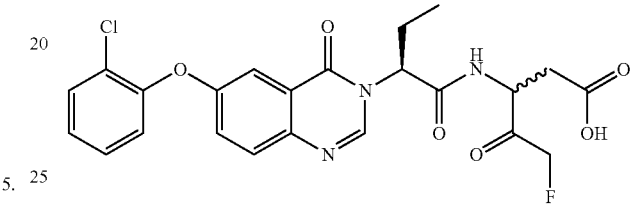

12.

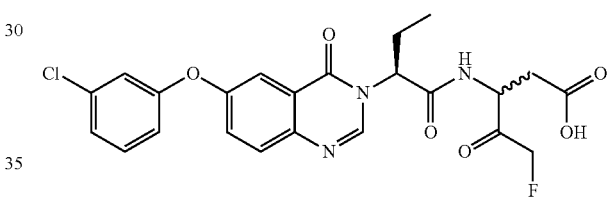

13.

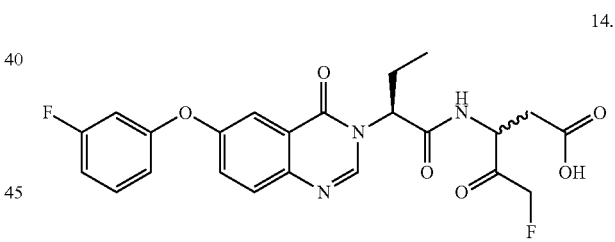

14.

15.

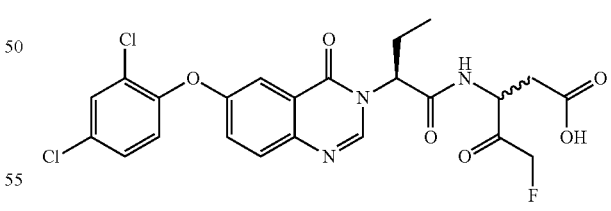

16.

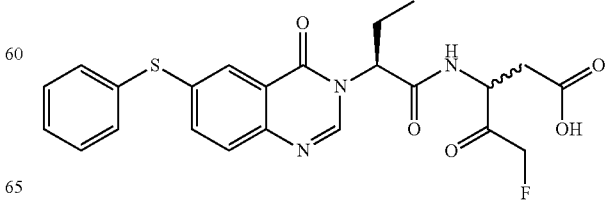

17. 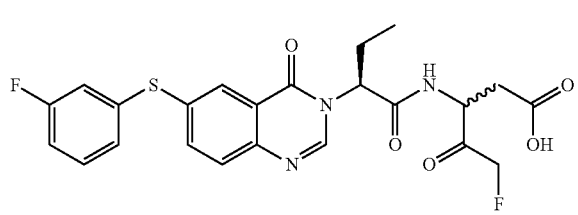
18. 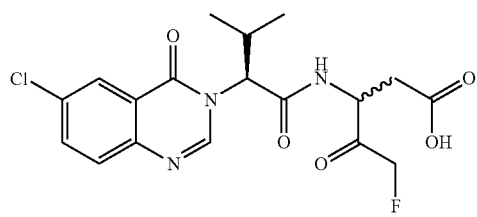
20. 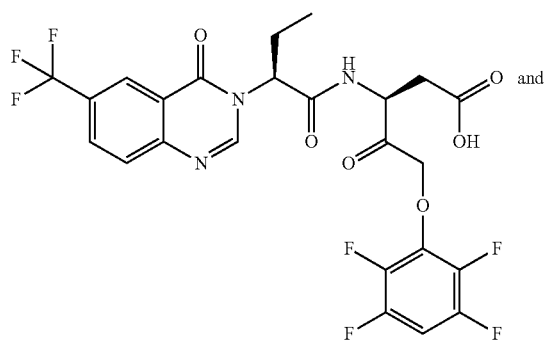
22. 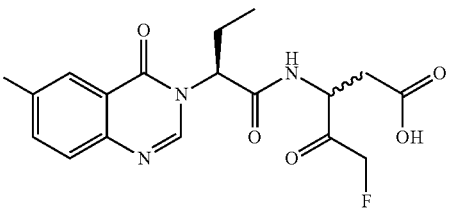
or a pharmaceutically acceptable salt thereof.
2. A pharmaceutical composition comprising:
a) a compound according to claim 1; and
b) a pharmaceutically acceptable carrier, adjuvant or vehicle.
* * * * *